United States Patent
Crowley et al.

(10) Patent No.: US 10,369,340 B2
(45) Date of Patent: Aug. 6, 2019

(54) DEVICE AND METHOD FOR SUSTAINED RELEASE OF LOW WATER SOLUBILITY THERAPEUTIC AGENT IN SOLUBILIZER

(71) Applicant: NANOMEDICAL SYSTEMS, INC., Austin, TX (US)

(72) Inventors: Michael Crowley, Austin, TX (US); Randy Goodall, Austin, TX (US); Lee Hudson, Elgin, TX (US)

(73) Assignee: NANOMEDICAL SYSTEMS, INC., Austin, TX (US)

( * ) Notice: Subject to any disclaimer, the term of this patent is extended or adjusted under 35 U.S.C. 154(b) by 135 days.

(21) Appl. No.: 14/908,157

(22) PCT Filed: Aug. 11, 2014

(86) PCT No.: PCT/US2014/050476
§ 371 (c)(1),
(2) Date: Jan. 28, 2016

(87) PCT Pub. No.: WO2015/023557
PCT Pub. Date: Feb. 19, 2015

(65) Prior Publication Data
US 2016/0175572 A1    Jun. 23, 2016

Related U.S. Application Data

(60) Provisional application No. 61/864,768, filed on Aug. 12, 2013.

(51) Int. Cl.
*A61K 9/00* (2006.01)
*A61M 31/00* (2006.01)
(Continued)

(52) U.S. Cl.
CPC ......... *A61M 31/002* (2013.01); *A61K 9/0024* (2013.01); *A61K 31/568* (2013.01);
(Continued)

(58) Field of Classification Search
CPC ..................... A61M 31/002; A61M 2205/04
See application file for complete search history.

(56) References Cited

U.S. PATENT DOCUMENTS 2,840,508 A    6/1958  Junkmann et al.
5,152,997 A   10/1992  Ebert et al.
(Continued)

FOREIGN PATENT DOCUMENTS

EP              1457208        6/2004
WO    WO 2003/101539   12/2003
(Continued)

OTHER PUBLICATIONS

Extended European Search Report issued in European Patent Application No. 1483681, dated Mar. 1, 2017.
(Continued)

*Primary Examiner* — Rebecca E Eisenberg
*Assistant Examiner* — Tasnim Mehjabin Ahmed
(74) *Attorney, Agent, or Firm* — Parker Highlander PLLC

(57) ABSTRACT

Devices and methods for administering a therapeutic agent, including an implantable delivery device. Exemplary embodiments include a reservoir in fluid communication with a channeled member, and a compound including the therapeutic agent and a solubilizer disposed within the reservoir.

12 Claims, 12 Drawing Sheets

(51) Int. Cl.
*A61K 47/22* (2006.01)
*A61K 47/44* (2017.01)
*A61K 31/568* (2006.01)
*A61K 31/569* (2006.01)
*A61K 47/14* (2017.01)

(52) U.S. Cl.
CPC ............ *A61K 31/569* (2013.01); *A61K 47/14* (2013.01); *A61K 47/22* (2013.01); *A61K 47/44* (2013.01); *A61M 2205/04* (2013.01)

(56) References Cited

U.S. PATENT DOCUMENTS

| | | | |
|---|---|---|---|
| 5,837,276 A | 11/1998 | Cheikh | |
| 2003/0064095 A1* | 4/2003 | Martin | A61K 9/0004 424/451 |
| 2007/0134305 A1* | 6/2007 | Zilberman | A61K 9/0024 424/443 |
| 2008/0208104 A1* | 8/2008 | Bragagna | A61B 18/203 604/20 |
| 2010/0152699 A1 | 6/2010 | Ferrari et al. | |
| 2011/0288497 A1* | 11/2011 | Goodall | A61L 27/306 604/264 |
| 2012/0059218 A1* | 3/2012 | Forsell | A61F 2/26 600/40 |
| 2013/0131628 A1 | 5/2013 | Grattoni et al. | |

FOREIGN PATENT DOCUMENTS

| | | |
|---|---|---|
| WO | WO 2011/146699 | 11/2011 |
| WO | WO 2013/112734 | 8/2013 |

OTHER PUBLICATIONS

PCT International Search Report and Written Opinion issued in International Application No. PCT/US2014/050476, dated Nov. 13, 2014.

* cited by examiner

Plasma concentration versus time curve for intravenous drug

DEVICE AND METHOD FOR SUSTAINED RELEASE OF LOW WATER SOLUBILITY THERAPEUTIC AGENT IN SOLUBILIZER

CROSS-REFERENCE TO RELATED APPLICATIONS

This application is a national phase application under 35 U.S.C. § 371 of International Application No. PCT/US2014/050476, filed Aug. 11, 2014, which claims priority to U.S. Provisional Patent Application Ser. No. 61/864,768, filed Aug. 12, 2013, the entire contents of each of the above-referenced disclosures are incorporated by reference herein.

BACKGROUND INFORMATION

Therapeutic agent (e.g. drug) delivery is an important aspect of medical treatment since the efficacy of a drug is directly related to its administration. Some therapies require repetitive drug administration to the patient over a long period of time, and in many cases long term consistent administration of drug is desirable. In addition, patient compliance with repetitive, long term drug administration can be an issue in some instances.

Considerable advances have been made in the field of drug delivery technology over the last three decades, resulting in many breakthroughs in clinical medicine. The creation of therapeutic agent delivery devices that are capable of delivering therapeutic agents in controlled ways still presents many challenges. One of the significant requirements for an implantable drug delivery device is controlled release of therapeutic agents, ranging from small drug molecules to larger biological molecules. In many instances, it is particularly desirable to achieve a continuous drug release profile whereby the concentration of drug in the bloodstream remains substantially constant throughout an extended delivery period. It can also be desirable for the implantable drug delivery device to provide continuous drug release via passive control mechanisms to minimize device complexity.

These devices have the potential to improve therapeutic efficacy, diminish life-threatening side effects, improve patient compliance, minimize the intervention of healthcare personnel, reduce the duration of hospital stays, and decrease the diversion and abuse of controlled substances.

By providing a more consistent release, it is possible to improve the therapeutic efficacy and simultaneously decrease the side effects (e.g. toxicity of temporary overdosing or diminished activity associated with a small drug concentration in the plasma) associated with multiple administrations of higher dosages.

The solubility of certain therapeutic agents can provide dosing and application challenges. For example, a therapeutic agent with poor water solubility requires a greater volume of solvent to dissolve the therapeutic agent in the injection or implantable delivery device in order to provide an effective dosing level for extended duration. In cases where it is desirable to have an extended dosing period, the volume of solvent and the dissolved therapeutic agent may be large, and therefore the implantable delivery device may be prohibitively large. Long term dosing of low solubility therapeutic agents in a small implantable delivery device is desirable.

In certain applications, implantable drug delivery devices may incorporate geometric constraints to provide for a controlled release rate of the therapeutic agent. For example, certain implantable drug delivery devices may utilize nanochannels to restrict the rate at which therapeutic molecules can diffuse from the device. In particular applications, geometric constraints can control the diffusion rate so that it is substantially independent of the concentration of the remaining therapeutic agent within the delivery device. These geometric constraints include nanochannels that are fabricated 2-5 times larger than the hydrodynamic size of the agent molecule. However, if the therapeutic molecule is sufficiently small, it can be difficult, if not impossible, to create a geometric constraint dimensioned to provide for a controlled release rate at a therapeutically-effective level. In addition, such small geometric constraints may lead to insufficient release of the agent.

The issues raised above are merely exemplary of the potential shortcomings of existing systems and are not intended to be an exhaustive listing of the issues addressed by embodiments of the present disclosure.

SUMMARY

Devices have recently been developed to address some of the issues described above. However, it was until recently believed that the environment within an implantable device should approximate the surrounding physiologic environment outside the device in order to facilitate administration of a therapeutic agent from the device. For example, previous efforts for therapeutic agent administration attempted to match the saline concentration of fluid inside the device to that of the outside environment in order to minimize boundary layers between the two environments and promote molecular diffusion of the therapeutic agents from the implantable device to the outside environment.

Recent efforts have discovered that in certain instances solubilizers within the device that do not approximate the surrounding environment can be successfully utilized. For example, certain oils have been found to effectively solubilize testosterone and testosterone esters to provide effective testosterone replacement therapy. It was previously believed that many oils would be effective at solubilizing therapeutic agents (including testosterone), but would not be effective at delivering the therapeutic agents to the patient. It is well known that oils are not miscible with water. This surprising result contradicted prevailing scientific understanding and literature publications which held that the boundary layer between the oil and saline environment would restrict or prevent a therapeutic agent from being effectively administered.

Exemplary embodiments of the present invention, however, utilize a therapeutic agent dissolved in a solubilizer that has relatively low miscibility with the outside environment in a reservoir of an implant that comprises channels to assist in controlling the release rate of the dissolved therapeutic agent. In particular embodiments, the implant may comprise nanochannels and/or microchannels.

In particular embodiments, the solubilizer may comprise one or more of the following: Gelucire 44/14, Gelucire 50/13, Peceol, Labrafil M2125 CS, Labrafil M1944 CS, Labrasol, Tween 80, Crodasol, Brij 30, Glycerox 767, NOVOL (Oleyl Alcohol), ETOCAS (PEG-35 Castor Oil), Arlosolve (Dimethyl lsosobride), PEG300, Maisine 35-1, Transcutol HP, Glycerin, Span 80, Span 85, Compritol 888, Propylene Glycol, Dibutyl Sebacate, Triacetin, Miglyol 810, Miglyol 812, Myvacet, Softigen 701, Softigen 767, Kolliphor HS15, Kolliphor RH40, Kolliphor ELP, Stearic Acid, Cetyl Palmitate, Lauroglycol 90, Lauroglycol FCC, Labrafac PG, Labrafac Lipophile WL 1349, Miranol, Soybean Oil, Corn Oil, Olive Oil, Castor Oil, Sesame Oil, Light Mineral Oil, Heavy Mineral Oil, Coconut Oil, Canola Oil, Dimethyl Sulfoxide (DMSO), N-Methylpyrrolidone (NMP), Benzyl Benzoate, Capryol 90, Capryol PGMC, Glyceryl Monostearate, Vitamin E TPGS and Benzyl Alcohol. This list is exemplary, and other appropriate solubilizers, cationic, anionic and nonionic surfactants, fatty acid esters, fatty acid alcohols, and other substances singularly or in combination known to those skilled in the art to enhance the aqueous solubility or provide for highly concentrated, low water miscibility suspensions of a target therapeutic agent within the device may be used. In specific embodiments, the solubilizer may be non-aqueous.

The inclusion of a concentrated therapeutic agent dissolved in a solubilizer within the reservoir can address several issues noted in existing systems. For example, portions of the solubilizer (with the dissolved therapeutic agent) that are small enough to pass through the channels can separate over time and be released to provide a more steady concentration of therapeutic agent. By providing a more steady concentration, rather than a concentration that is initially high and subsequently reduced (as might be the case for therapeutic agent delivery outside the constrained reservoir), the geometry of the delivery device can be optimized. For example, it may be possible to increase the size of the channels because the concentration of the reservoir is maintained at a more steady level by the presence of the non-miscible therapeutic agent, so less geometric constraint is required. Also, one or more dimensions of the portions of the solubilizer (with the dissolved therapeutic agent) that break away can be tens or hundreds of nanometers, so that channeled members with geometrics constraints, e.g., nanochannels having dimensions the size range 50 to 250 nanometers, can regulate the release of these portions.

The use of a therapeutic agent dissolved in a solubilizer may also make it possible to administer therapeutic agents that would otherwise be difficult to administer consistently at therapeutic levels with a variable-concentration reservoir and a channeled member.

Exemplary embodiments of the present disclosure comprise an implantable device comprising a reservoir, a channeled member in fluid communication with the reservoir; and a compound comprising a therapeutic agent and a solubilizer disposed within the reservoir and in fluid communication with the channeled member.

Certain embodiments may include a device for administering a therapeutic agent, where the device comprises: an implantable device comprising a reservoir; a channeled member in fluid communication with the reservoir; and a compound comprising the therapeutic agent and a solubilizer disposed within the reservoir and in fluid communication with the channeled member.

In specific embodiments the compound may comprise testosterone or a testosterone ether, ester, or salt. In particular embodiments, the compound may comprise testosterone enanthate, testosterone cypionate, testosterone propionate, testosterone decanoate, and/or methyltestosterone. In certain embodiments, the solubilizer may comprise an oil. In particular embodiments, the solubilizer may be non-aqueous.

In specific embodiments, the solubilizer may comprise at least one of: Gelucire 44/14, Gelucire 50/13, Peceol, Labrafil M2125 CS, Labrafil M1944 CS, Labrasol, Tween 80, Crodasol, Brij 30, Glycerox 767, NOVOL (Oleyl Alcohol), ETOCAS (PEG-35 Castor Oil), Arlosolve (Dimethyl lsosobride), PEG300, Maisine 35-1, Transcutol HP, Glycerin, Span 80, Span 85, Compritol 888, Propylene Glycol, Dibutyl Sebacate, Triacetin, Miglyol 810, Miglyol 812, Myvacet, Softigen 701, Softigen 767, Kolliphor HS15, Kolliphor RH40, Kolliphor ELP, Stearic Acid, Cetyl Palmitate, Lauroglycol 90, Lauroglycol FCC, Labrafac PG, Labrafac Lipophile WL 1349, Miranol, soybean oil, corn oil, olive oil, castor oil, sesame oil, light mineral oil, heavy mineral oil, coconut oil, canola oil, dimethyl sulfoxide (DMSO), N-Methylpyrrolidone (NMP), Benzyl Benzoate, Capryol PGMC, Glyceryl Monostearate, Vitamin E TPGS and Benzyl Alcohol.

In certain embodiments, the channeled member may comprise a nanochannel. In specific embodiments, the nanochannel may have a dimension of up to 50 nm, or have a dimension in the range of 50-100 nm; 100-150 nm; 150-170 nm; 170-190 nm; 190-210 nm; 210-225 nm; 225-240 nm; or 240-250 nm. In particular embodiments, the channeled member may comprise microchannels. In certain embodiments, the device may comprise an injection port and/or a vent.

Specific embodiments include a method of administering a therapeutic agent, where the method may comprise: inserting a device as disclosed herein into an area of a human or animal anatomy (where the device comprises: a reservoir; a channeled member in fluid communication with the reservoir; and a compound comprising the therapeutic agent and a solubilizer disposed within the reservoir and in fluid communication with the channeled member); and releasing at least a portion of the therapeutic agent from the device into the area of the human or animal anatomy.

In certain embodiments of the method, the device may be configured to release the therapeutic agent at a substantially constant release rate for a dosage period of at least one week, of at least one month, of at least six months, or of at least one year.

In specific embodiments of the method, the compound may comprise testosterone or a testosterone ether, ester, or salt. In particular embodiments of the method, the compound may comprise testosterone enanthate, testosterone cypionate, testosterone propionate, testosterone decanoate, and/or methyltestosterone. In certain embodiments of the method, solubilizer may comprise an oil. In particular embodiments of the method, the solubilizer may be non-aqueous.

In specific embodiments of the method, the solubilizer may comprise at least one of: Gelucire 44/14, Gelucire 50/13, Peceol, Labrafil M2125 CS, Labrafil M1944 CS, Labrasol, Tween 80, Crodasol, Brij 30, Glycerox 767, NOVOL (Oleyl Alcohol), ETOCAS (PEG-35 Castor Oil), Arlosolve (Dimethyl lsosobride), PEG300, Maisine 35-1, Transcutol HP, Glycerin, Span 80, Span 85, Compritol 888, Propylene Glycol, Dibutyl Sebacate, Triacetin, Miglyol 810, Miglyol 812, Myvacet, Softigen 701, Softigen 767, Kolliphor HS15, Kolliphor RH40, Kolliphor ELP, Stearic Acid, Cetyl Palmitate, Lauroglycol 90, Lauroglycol FCC, Labrafac PG, Labrafac Lipophile WL 1349, Miranol, soybean oil, corn oil, olive oil, castor oil, sesame oil, light mineral oil, heavy mineral oil, coconut oil, canola oil, dimethyl sulfoxide (DMSO), N-Methylpyrrolidone (NMP), Benzyl Benzoate, Capryol PGMC, Glyceryl Monostearate, Vitamin E TPGS and Benzyl Alcohol.

In certain embodiments of the method, the channeled member may comprise a nanochannel. In specific embodiments, the nanochannel may have a dimension of up to 50 nm, or have a dimension in the range of 50-100 nm; 100-150 nm; 150-170 nm; 170-190 nm; 190-210 nm; 210-225 nm; 225-240 nm; or 240-250 nm. In particular embodiments of the method, the channeled member may comprise microchannels. In certain embodiments of the method, the device may comprise an injection port and/or a vent.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 10%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The term "channeled member" as used herein includes structures comprising microchannels and/or nanochannels, including not limited to, any of the exemplary nanochannel devices disclosed in U.S. patent application Ser. No. 12/618,233 filed Nov. 13, 2009 (U.S. Patent Publication 20100152699) and entitled "Nanochanneled Device and Related Methods" and International Patent Application Number PCT/US10/30937 (WIPO Patent Publication WO/2011/146699) filed Apr. 13, 2010 and entitled "Nanochanneled Device and Method of Use", both of which are incorporated herein by reference.

The term "microchannel" is defined as a channel with a cross-section having at least one dimension (e.g. height, width, diameter, etc.) that is greater than 500 nm and less than 50 µm.

The term "nanochannel" is defined as a channel with a cross-section having at least one dimension (e.g. height, width, diameter, etc.) that is less than 500 nm.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF EXEMPLARY EMBODIMENTS

Figure 1:
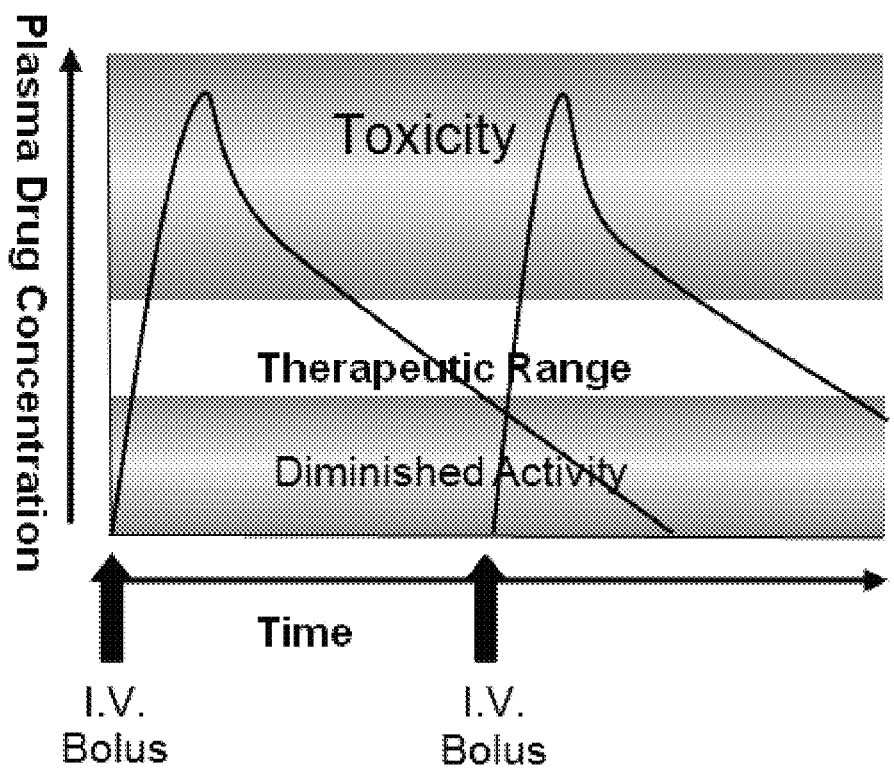
FIG. 1 is a graph that illustrates a plasma drug concentration over time when the drug is administered via traditional intravenous (IV) methods.

As previously mentioned, a more constant drug administration can provide numerous advantages over periodic administrations that are initially above the therapeutic range and subsequently diminish to below the therapeutic range. Referring to FIG. 1, a graph illustrates plasma drug concentration versus time in one example of a typical conventional drug administration utilizing period dosage. As illustrated in FIG. 1, the drug concentration is initially significantly above the therapeutic range and subsequently reduces to a level below the therapeutic range. When the concentration is reduced to a level below the therapeutic range, another dosage can be administered and the drug concentration again exceeds the therapeutic range before being reduced into the desired therapeutic range.

Figure 2:
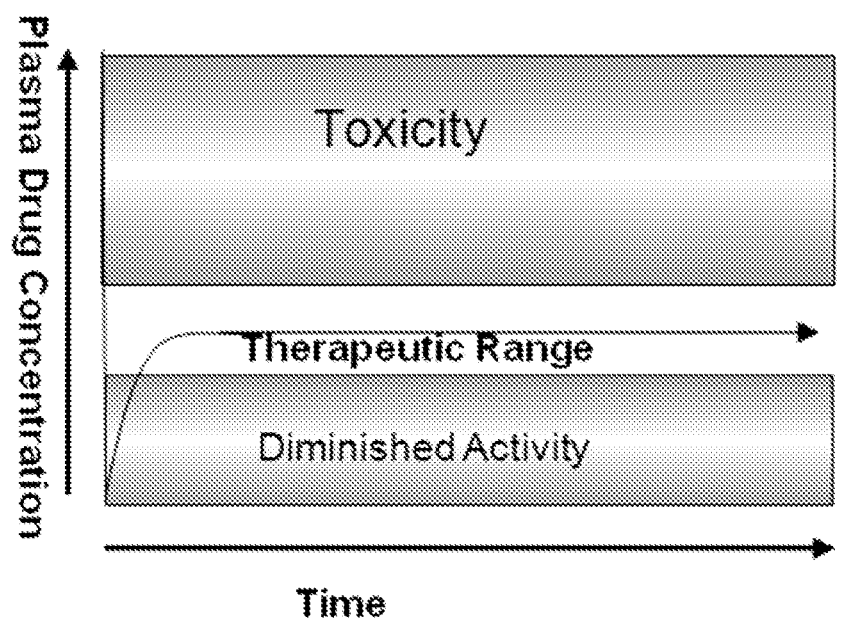
FIG. 2 is a graph that illustrates a plasma drug concentration over time when the drug is administered via a therapeutic agent and solubilizer in an implantable delivery device.

FIG. 2 shows the plasma drug concentration (PDC) over time when the drug is administered via a solid matter therapeutic agent in an implantable delivery device, as described in more detail below. The employment of a solid matter therapeutic agent in an implantable delivery device for constant drug release can improve the efficacy of the treatment. In addition it can avoid frequent injections and, in many cases, reduce or solve the issues of patient compliance.

Figure 3:
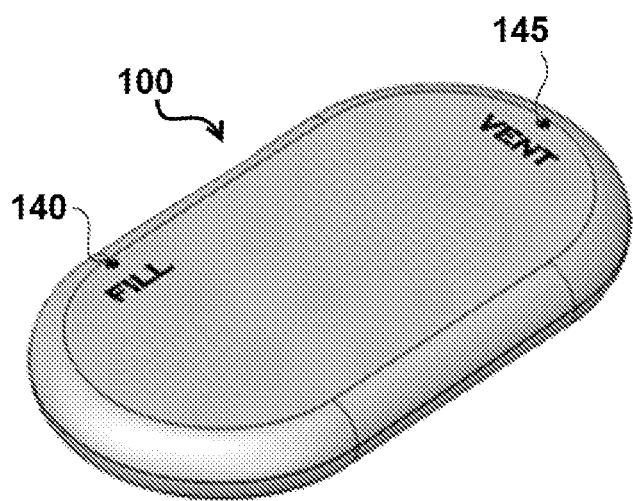
FIG. 3 is a top perspective view of an implantable delivery device.
Figure 4:
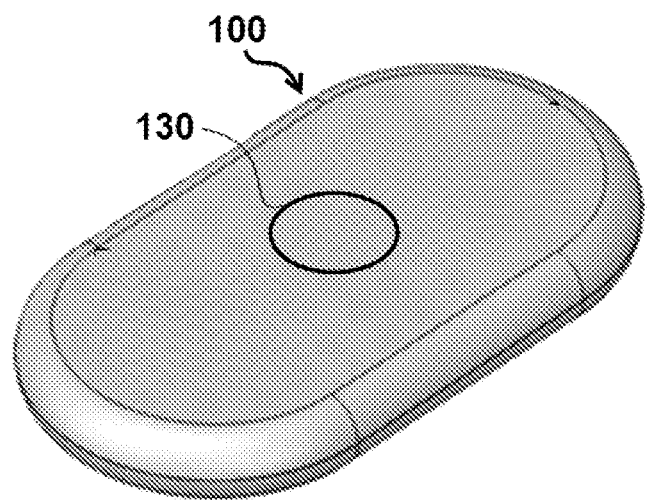
FIG. 4 is a bottom perspective view of an implantable delivery device.
Figure 5:
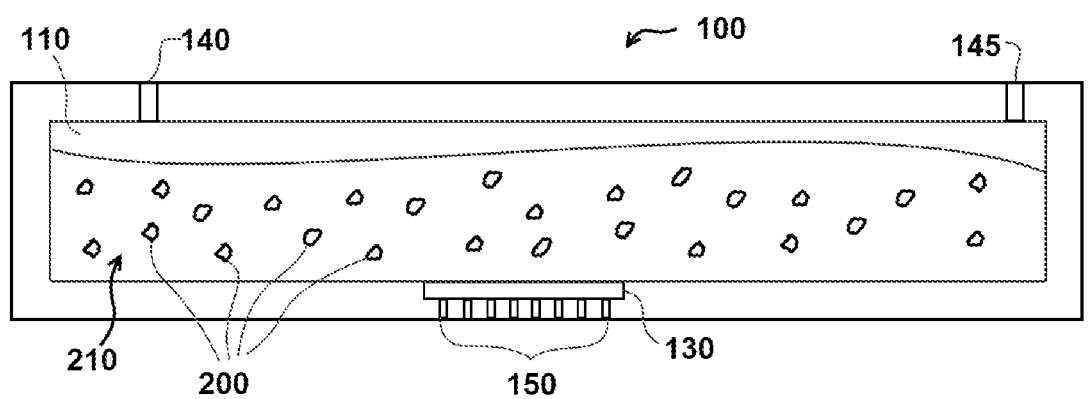
FIG. 5 is a section view of the embodiment of FIG. 3.

Referring now to FIGS. 3-5, an implantable delivery device (IDD) 100 is shown in perspective views (FIGS. 3 and 4) and a sectional view (FIG. 5). It is understood that the figures shown are not to scale and are intended for representative purposes only. In this embodiment, IDD 100 comprises a reservoir 110 with a channeled member 130. In the exemplary embodiment shown, IDD 100 also comprises an injection port 140, a vent 145 and exit ports 150. In particular embodiments, the injection port 140 and vent port 145 are filled with a substance, for example, silicone rubber, and the channeled member 130 is in fluid communication with the exit ports 150. In particular embodiments, IDD 100 may be formed from suitable bio-compatible materials including for example Polyether ether ketone (PEEK) or titanium.

In particular embodiments, channeled member 130 may comprise microchannels, and in specific embodiments, channeled member 130 may comprise nanochannels. Channeled member 130 may also comprise both microchannels and nanochannels in certain embodiments. In some embodiments, channeled member 130 may be an integral component of IDD 100, while in other embodiments, channeled member 130 may be a separate component that is coupled to or inserted into IDD 100. In particular embodiments, channeled member 130 may have a surface area of less than 1 cm$^2$ exposed to reservoir 110, and in specific embodiments may comprise a surface area of approximately 0.75 cm$^2$ exposed to reservoir 110. In certain embodiments, channeled member 130 may be approximately 6 mm×6 mm.

Figure 6:
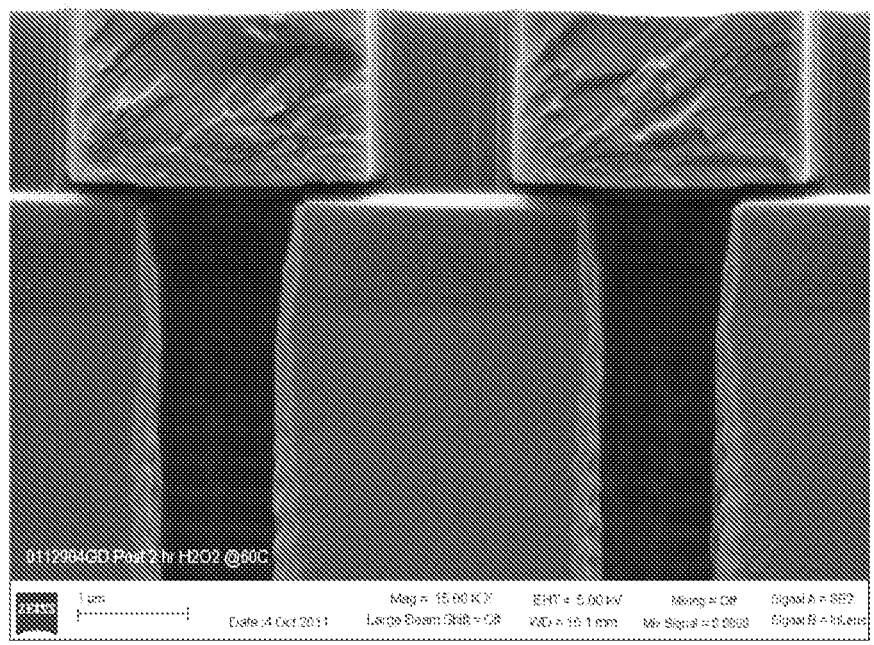
FIG. 6 is a scanning electron microscope (SEM) cross-section image of a portion of a channeled member of FIG. 3.
Figure 7:
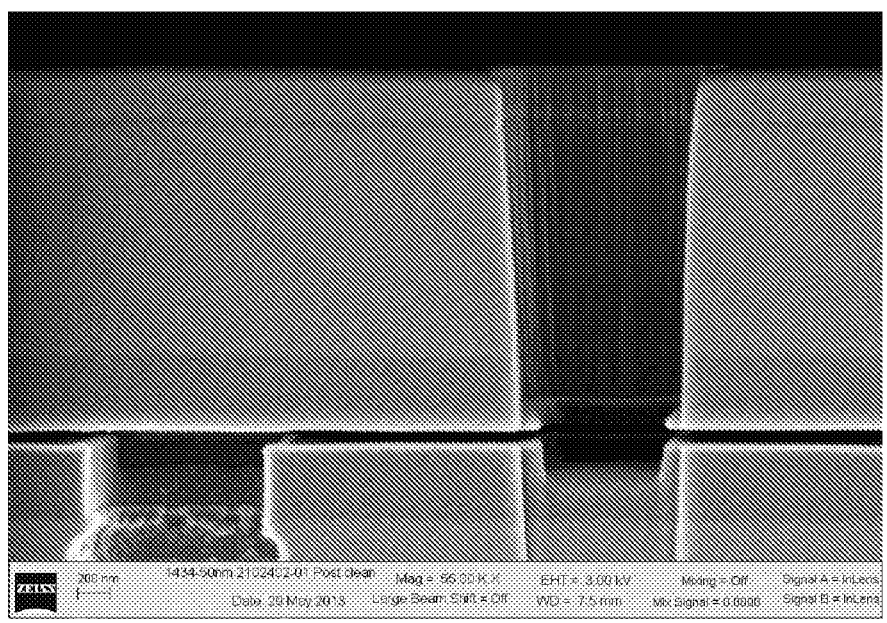
FIG. 7 is a scanning electron microscope (SEM) cross-section image of a portion of a channeled member of FIG. 3.

In particular embodiments, channeled member 130 may be equivalent to the nanochannel delivery device (and may be constructed via the associated methods) disclosed within in U.S. Patent Publication 20100152699, incorporated herein by reference. In other embodiments, channeled member 130 may comprise microchannels without nanochannels. In certain embodiments, channeled member 130 may comprise one or more coatings compatible with in vivo use, including for example, coating as described in U.S. Patent Publication 20110288497. Referring now to FIGS. 6 and 7, scanning electron microscope (SEM) images of a portion of a channeled member are shown after in vivo testing without a coating (FIG. 6) and with a coating (FIG. 7).

In exemplary embodiments, reservoir 110 can be filled with an active pharmaceutical ingredient (API) 200 dissolved in a solubilizer 210. In particular embodiments, API 200 may comprise, for example, testosterone or a testosterone ester and solubilizer 210 may comprise one or more of the compounds listed above in the Summary section of this disclosure.

During use, IDD 100 can be used to administer API 200 by inserting IDD 100 into an area of a human anatomy, including for example, subcutaneously. With IDD 100 inserted into the desired anatomical area, portions of solubilizer 210 (with dissolved API 200) that are small enough to pass through channeled member 130 can be released over time into the area of the human anatomy or for systemic circulation. In certain embodiments, the solubility enhancement of API 200 and solubilizer 210 can range from approximately 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30× or higher. In particular embodiments, the solubility enhancement can be up to 1000× and higher. For example, with testosterone the native water solubility is 35 µg/ml, but in ethanol it is approximately 750 mg/ml, which is a 20,000× increase.

In certain embodiments, IDD 100 and channeled member 130 can be configured to release up to approximately 3, 4, 5, 6, 7, 8, 9 or 10 mg of API 200 per day over a period of time up 12 months. In other embodiments, IDD 100 may be configured to release a different dosage over shorter or longer periods of time. For example, in particular embodiments IDD 100 can be configured to release 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8 or 2.9 mg/day of API 200. IDD 100 can also be configured to release API 200 over a matter of 1, 3, 4, 5, 6, or 7 days, 1, 2, 3, or 4 weeks, or 1, 2, 3, 4, 5, 6, 7, 8, 9, 10, 11, 12 months. In certain exemplary embodiments, IDD 100 can be configured to release between approximately 1 gm and 2 gm of API 200 over a period of approximately 12 months. In particular embodiments, IDD 100 and channeled member 130 can be configured to release between approximately 200-700 µg/day/cm$^2$ (as measured at the surface area of the channeled member exposed to reservoir 110).

In particular embodiments, therapeutic agent may comprise one or more of the following substances: testosterone, testosterone esters (including but not limited to testosterone enanthate, testosterone cypionate, testosterone propionate, and methyltestosterone). Many other therapeutic agents and other substances known to have low solubility in water may be used in the manner of this disclosure.

FIGS. 6 and 7 show an SEM cross-section image of a portion of a channeled member, including microchannels in fluid communication with nanochannels of height 200 nm and 50 nm, respectively.

Figure 8:
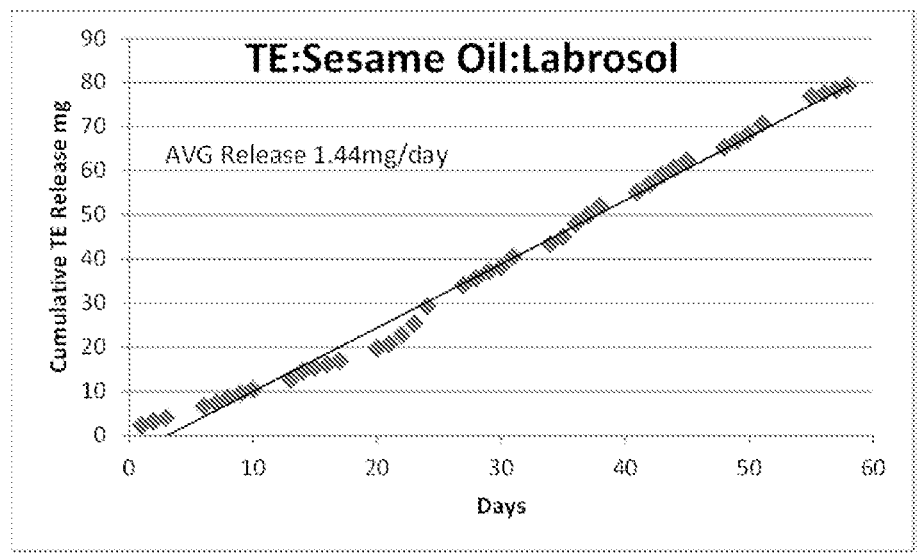
FIG. 8 is a graph of a cumulative release rate of testosterone enanthate (TE) from a channeled member in combination with sesame oil and Labrasol.
Figure 9:
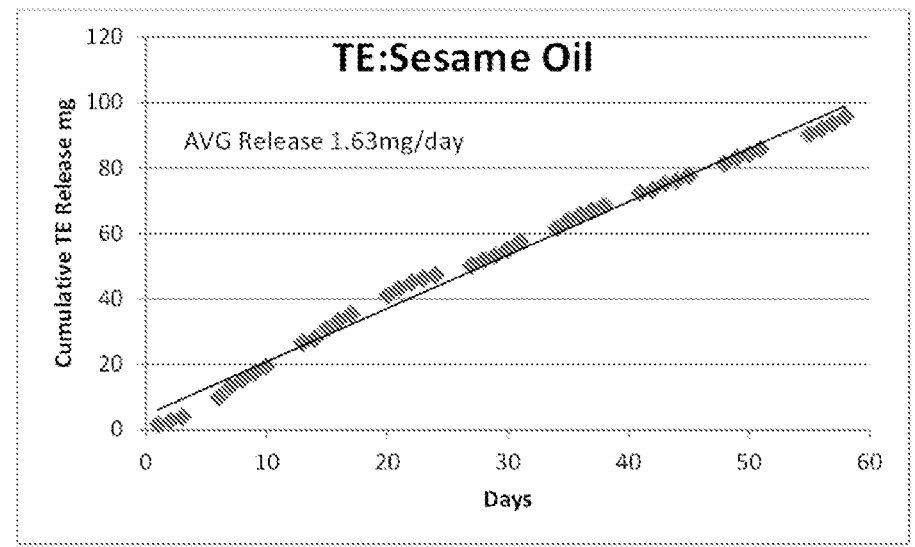
FIG. 9 is a graph of a cumulative release rate of testosterone enanthate (TE) from a channeled member in combination with sesame oil.
Figure 10:
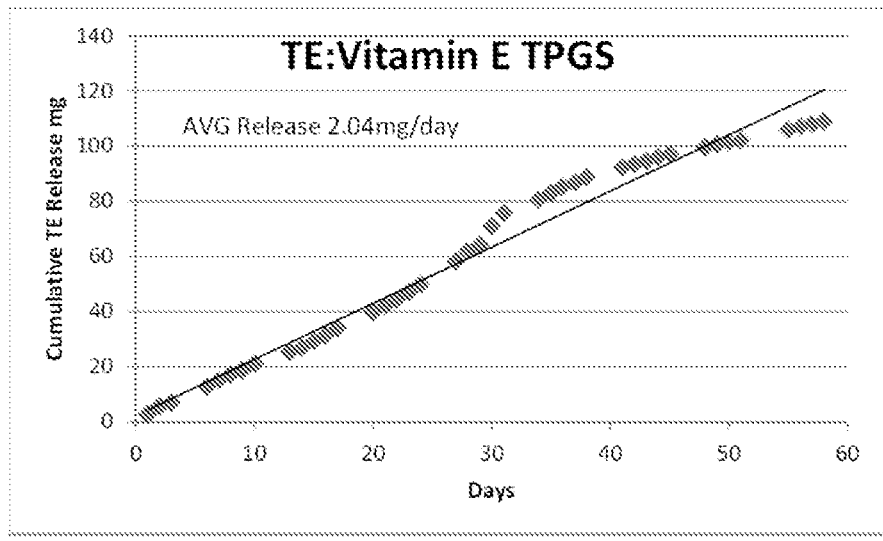
FIG. 10 is a graph of a cumulative release rate of testosterone enanthate (TE) from a channeled member in combination with Vitamin E TPGS.
Figure 11:
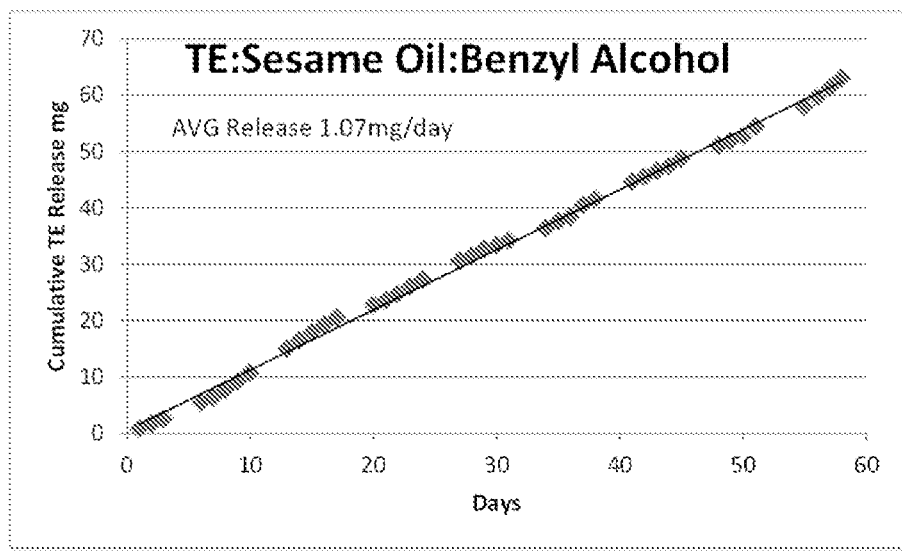
FIG. 11 is a graph of a cumulative release rate of testosterone enanthate (TE) from a channeled member in combination with sesame oil and benzyl alcohol.
Figure 12:
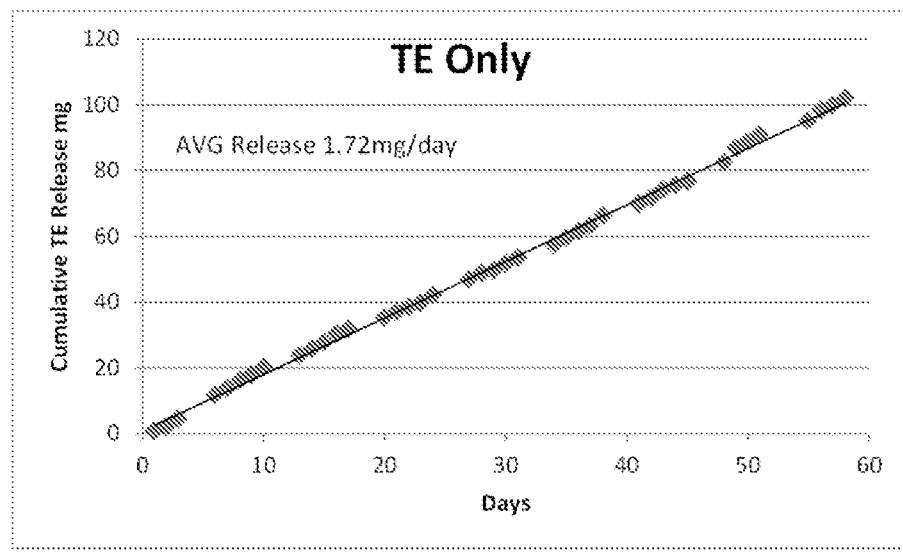
FIG. 12 is a graph of a cumulative release rate of testosterone enanthate (TE) from a channeled member.
Figure 13:
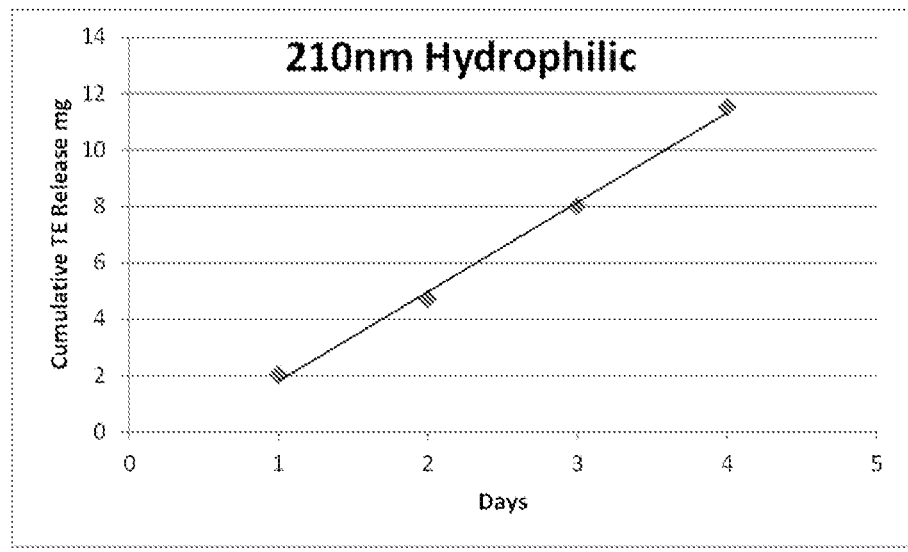
FIGS. 13-21 are graphs of a cumulative release rate of testosterone enanthate (TE) from a channeled member of with nanochannel heights of 160 nm, 190 nm, 200 nm, 210 nm, 220 nm, and 250 nm, and with and without a hydrophilic surface treatment included.
Figure 14:
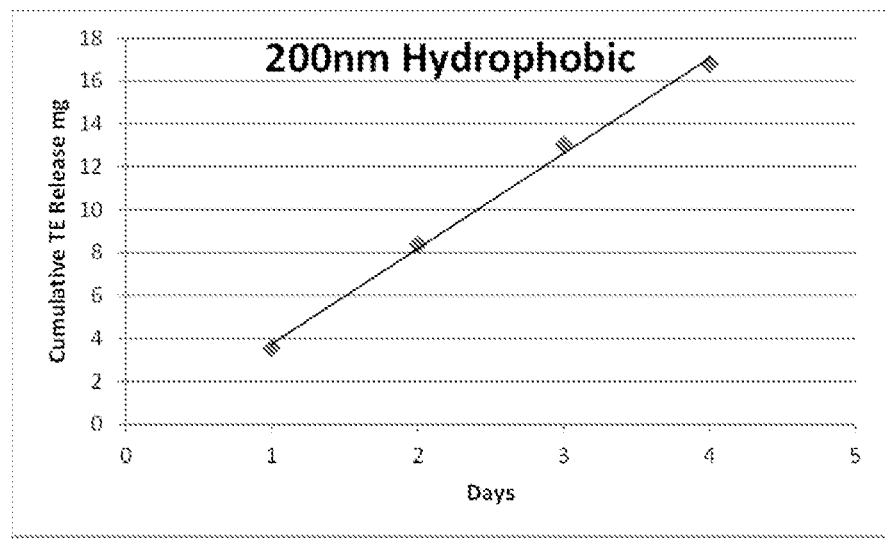
Figure 15:
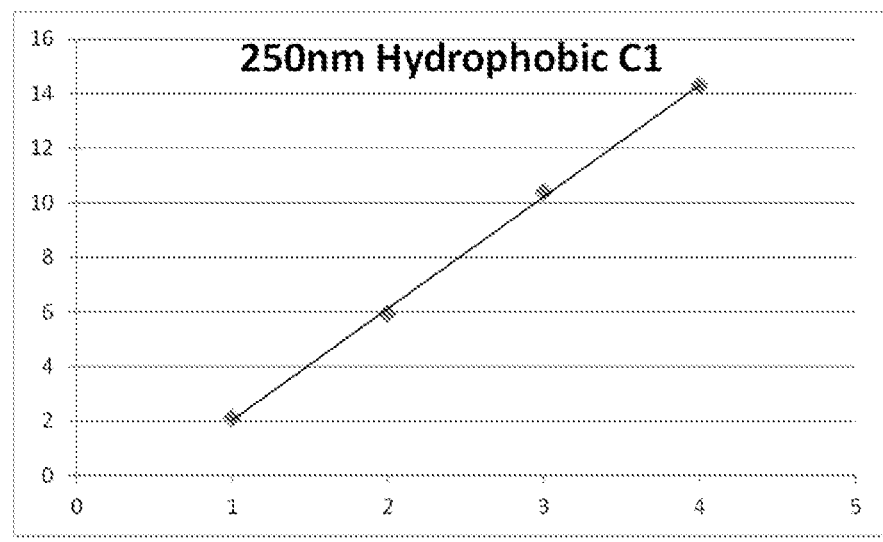
Figure 16:
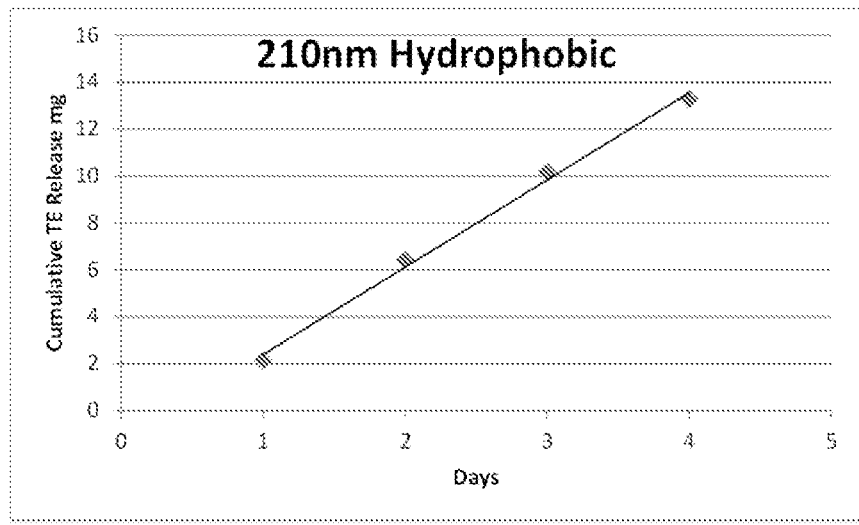
Figure 17:
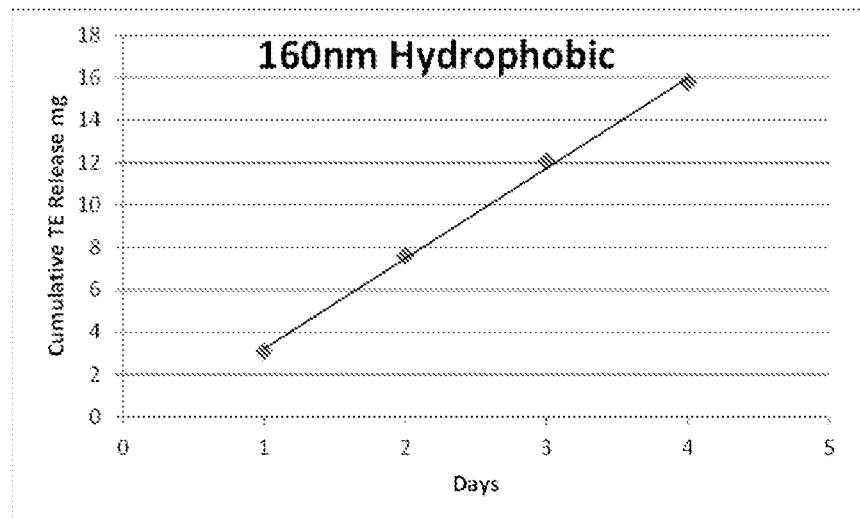
Figure 18:
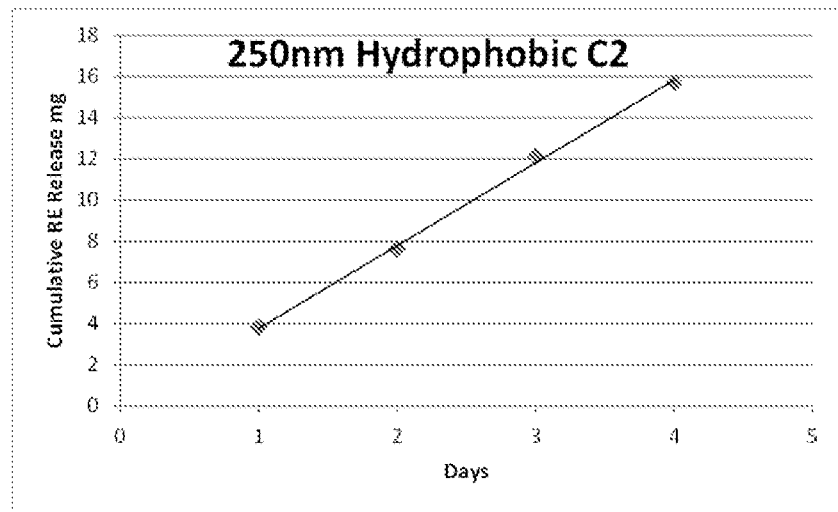
Figure 19:
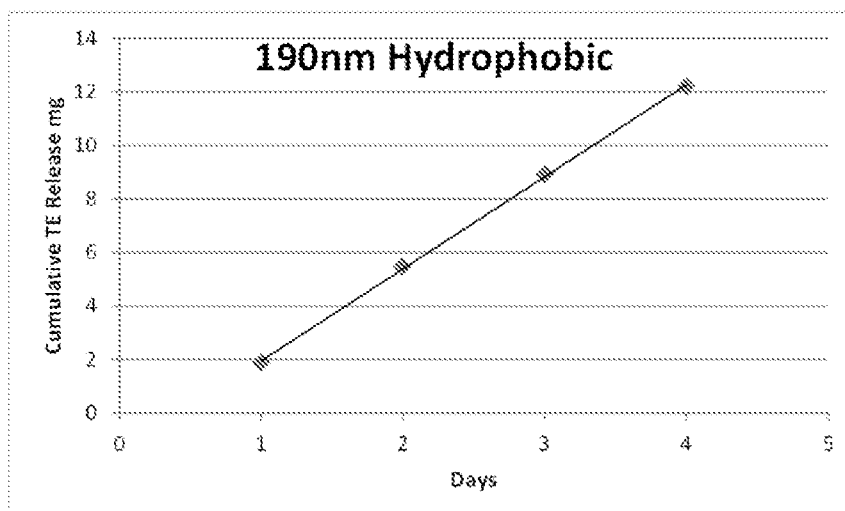
Figure 20:
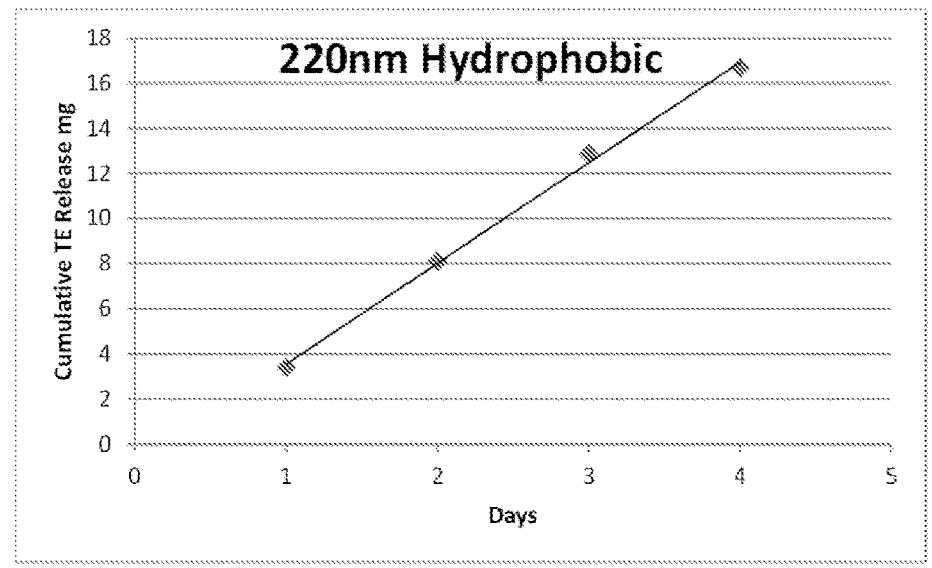
Figure 21:
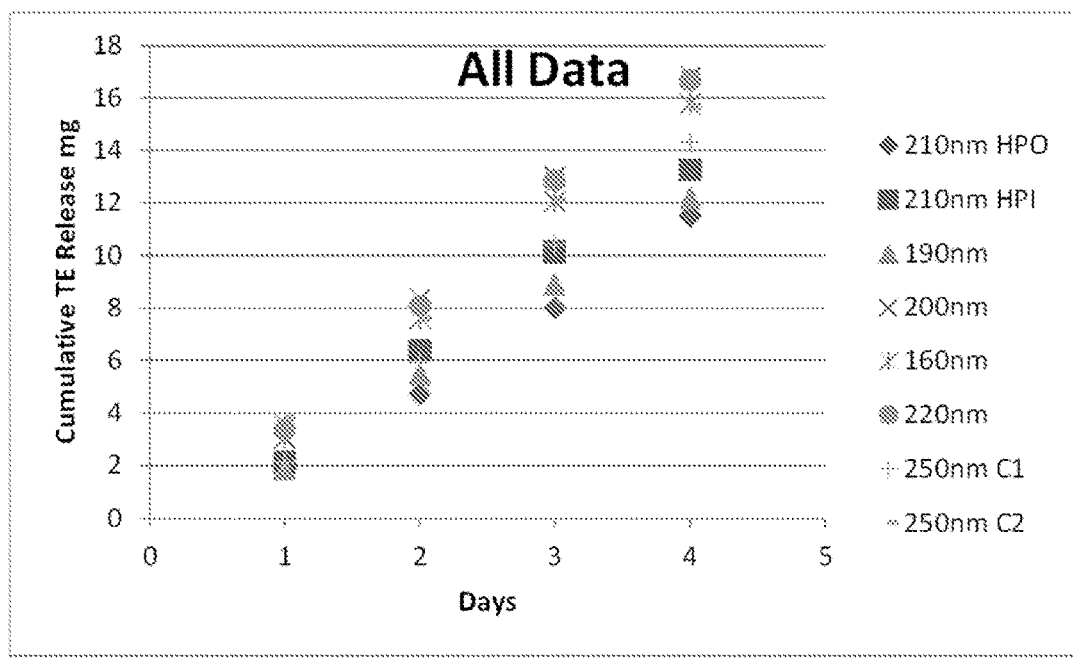

FIG. 8 is a graph of a cumulative release rate of testosterone enanthate (TE) from a channeled member in combination with sesame oil and Labrasol in an 8:1:1 ratio of TE/sesame oil/Labrasol. FIG. 9 is a graph of a cumulative release rate of TE and sesame oil in a 9:1 ratio, while FIG. 10 is a graph of TE and Vitamin E TPGS in a 9:1 ratio. FIG. 11 is a graph of a cumulative release rate of TE/sesame oil/benzyl alcohol in an 8:1:1 ratio. FIG. 12 is a graph of a cumulative release rate of only TE from a channeled member. During testing, capsules containing 200 µl of formulation were placed in a 250 ml sink volume held at 37 degrees C. The sink condition was maintained with 3% added Labrosol, and the sink solution was replaced at each sampling time to maintain sink conditions. A constant release with average rates of approximately 1.1 mg-2.4 mg per day observed in all samples.

FIGS. 13-21 are graphs of a cumulative release rate of testosterone enanthate (TE) from a channeled member of with nanochannel heights of 160 nm, 190 nm, 200 nm, 210 nm, 220 nm, and 250 nm, and with and without a hydrophilic surface treatment included. During testing, capsules containing 200 µl of formulation were again placed in a 250 ml sink volume held at 37 degrees C. The sink condition was maintained with 3% added Labrosol, and the sink solution was replaced at each sampling time to maintain sink conditions. It is a surprising result of this disclosure that immiscible formulations within the reservoir have a diffusion rate that has low sensitivity to both nanochannel height and to hydrophobic/hydrophilic surface. This novel result of combining a channeled member with a solubilizer significantly adds to the utility and range of application of this disclosure.

Figure 22:
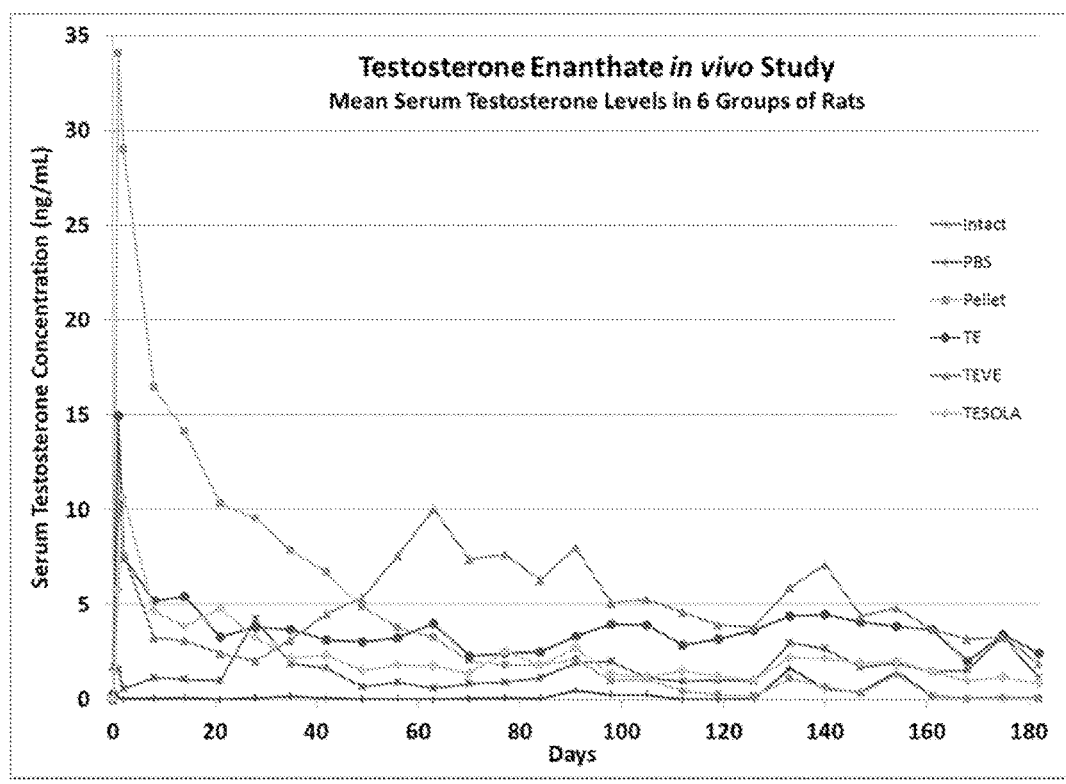
FIG. 22 is a graph of a concentration of testosterone serum in vivo.

FIG. 22 is a graph of serum concentration of testosterone in vivo. Three formulations were used: TE, TE:Sesame Oil:Labrosol and TE:Vitamin E TPGS. As shown in the legend, the test subjects included intact rats (Intact), castrated rats treated with a solid testosterone pellet implant (Pellet), castrated rats treated with a saline-filled implant (PBS), castrated rats treated with TE-only implants (TE), castrated rats with TE:sesame oil:labrosol (8:1:1) (TESOLA), and castrated rats with TE:Vitamin E TPGS (9:1) (TEVE). The formulations according to this disclosure are observed to provide significant testosterone serum levels while avoiding the typical "burst effect" observed in other implants and injections.

In particular embodiments, the therapeutic agent may comprise one or more of the following substances: adrenergic agent; adrenocortical steroid; adrenocortical suppressant; aldosterone; alkylating agent; antagonist; amino acid; anabolic; analeptic; analgesic; analgesic agonists and antagonists; anesthetic; anorexogenic; anti-acne agent; anti-adrenergic; anti-allergic; anti-alopecia agent; anti-amebic; anti-anemic; anti-anginal; antiangiogenic, anti-anxiety; anti-arthritic; anti-asthmatic; anti-atherosclerotic; antibacterial; antibiotic; anticancer; anticholinergic; anticoagulant; anticonvulsant; antidepressant; antidiabetic; antidiarrheal; antidiuretic; anti-dyskinetic; anti-emetic; anti-epileptic; antifibrinolytic; antifungal; anti-hemorrhagic; antihistamine; anti-hypercalcemic, anti-hypercholesterolaemic; anti-hyperlipidaemic; anti-hypertensive; anti-hypertriglyceridemic; anti-hypotensive; anti-infective; anti-inflammatory; anti-ischemic; antimicrobial; antimigraine; antimitotic; antimycotic; anti-nauseant; anti-neoplastic; anti-neutropenic; anti-obesity agent; anti-osteoporotic, antiparasitic; antiproliferative; antipsychotic; antiretroviral; anti-resorptives; anti-rheumatic; anti-seborrheic; antisecretory; antispasmodic; antisclerotic; antithrombotic; antitumor; anti-ulcerative; antiviral; appetite suppressant; bisphosphonate; blood glucose regulator; bronchodilator; cardiovascular agent; central nervous system agent; contraceptive; cholinergic; concentration aid; depressant; diagnostic aid; diuretic; DNA-containing agent, dopaminergic agent; estrogen receptor agonist; fertility agent; fibrinolytic; fluorescent agent; free oxygen radical scavenger; gastric acid suppressant; gastrointestinal motility effector; glucocorticoid; glutamatergic agent; hair growth stimulant; hemostatic; histamine H2 receptor antagonist; hormone; hypo cholesterolemic; hypoglycemic; hypolipidemic; hypotensive; imaging agent; immunizing agent; immunomodulator; immunostimulant; immunosuppressant; interleukin, keratolytic; LHRH agonist; mood regulator; mucolytic; mydriatic; nasal decongestant; neuromuscular blocking agent; neuroprotective; NMDA antagonist; non-hormonal sterol derivative; nootropic agent; opioids; parasympathomimetic agent; plasminogen activator; platelet activating factor antagonist; platelet aggregation inhibitor; platinum-containing agent, psychotropic; radioactive agent; raf antagonist, RNA-containing agent, scabicide; sclerosing agent; sedative; sedative-hypnotic; selective adenosine A1 antagonist; selective estrogen receptor modulator, serotonin antagonist; serotonin inhibitor; serotonin receptor antagonist; steroid; stimulant; thrombic agent; thyroid hormone; thyroid inhibitor; thyromimetic; tranquilizer; vasoconstrictor; vasodilator; wound healing agent; xanthine oxidase inhibitor; and the like; Abacavir, Abacavir sulfate, abatacept, Acarbose, Acetaminophen, Aciclovir, Adalimumab, Adapalene, Alendronate, Alendronate sodium, Alfuzosin, aliskiren, allopurinol, alvimopan, ambrisentan, Aminocaproic acid, Amitriptyline hydrochloride, amlodipine, amlodipine besylate, amoxicillin, amoxicilline, Amphetamine, Anastrozole, Aripiprazole, armodafinil, Atazanavir, atenolol, Atomoxetine, atorvastatin calcium, atorvastatin, Atropine sulfate, Azelastine, azithromycin, Balsalazide, Benazepril, bendamustine hydrochloride, Benzepril hydrochloride, bevacizumab, Bicalutamide, Bimatoprost, Bisoprolol, Bisoprolol fumarate, Bosentan, Botulin toxin, Budesonide, Buformin, Buprenorphine, Bupropion, bupropion hydrobromide, Bupropion Hydrochloride, Cabergoline, Calcipotriol, calcitriol, candesartan cilexetil, Capecitabine, Captopril, carbidopa, carisoprodol, Carvedilol, Caspofungin, Cefdinir, Cefoperazone, Cefotiam, cefprozil, Cefuroxime, Celecoxib, cephalaxin, Certolizumab Pegol, Cetirizine, Cetrizine hydrochloride, Cetuximab, Chlorpromazine hydrochloride, Chlorpheniramine maleate, ciclesonide, Cilastatin, cimetidine, Cinacalcet, Ciprofloxacin, citalopram hydrobromide, Clarithromycin, Clindamycin, Clindamycin, clindamycin hydrochloride, Clomipramine hydrochloride, Clonidine hydrochloride, clopidogrel, Clopidogrel bisulfate, Cloxacillin Sodium, Co-Amoxiclav, Codeine phosphate, Colchicines, Colesevelam, cyclobenzaprine hydrochloride, Cyclophosphamide, Cyclosporine, darbepoetin alfa, Darifenacin, DCRM 197 protein, Desloratadine, desloratidine, Desmopressin sulfate, Desoximetasone, dexamethasone, Diclofenac, Diethylcarbamazine citrate, difluprednate, diphenhydramine, Dipyridamole, DL-methionine, Docetaxel, Donepezil, doripenem, Dorzolamide, Doxazosin, doxazosin mesylate, doxycydine, Drospirenone, Duloxetine, Dutasteride, eculizumab, Efavirenz, Emtricitabine, Enalapril, enalapril maleate, Enoxaparin Sodium, Eprosartan, Erlotinib, Erythromycin, Erythropoetin, Escitalopram, esomeprazole, estradiol, Estrogen, Eszopiclone, etanercept, Ethembutol hydrochloride, Ethosuximide, ethynl estradiol, etonogestrel, etoricoxib, etravirine, Exenatide, Ezetimibe, Ezetimibe, Factor VII, famotidine, Famotidine, Fenofibrate, Fenofibrate, Fentanyl, Fentanyl citrate, Ferrous sulfate, Fexofenadine, fexofenadine hydrochloride, Filgrastim, Finasteride, fluconazole, Fluoxetine hydrochloride, Fluticasone, Fluvastatin, folic acid, Follitropin alfa, Follitropin beta, Formoterol, Fosinopril sodium, Gabapentin, Gabapentin, Gemcitabine, glargine insulin, Glatiramer, glimepride, Goserelin, histrelin acetate, Human growth hormone, Hydralazine hydrochloride, Hydrocodone bitartrate, Hydroxyurea, Hydroxyzine hydrochloride, Ibandronate, Imatinib, Imiglucerase, Imipenem, imiquimod, Indinavir sulfate, infliximab, Interferon beta-1a, Ipratropium, Irbesartan, Irinotecan, Isoniazid, Isosorbide moninitrate, ixabepilone, ketamine, ketoconazole, Ketorolac, Lactobionate, Lamivudine, Lamivudine, Lamotrigine, lanreotide acetate, Lansoprazole, lapatinib, laropiprant, Latanoprost, Letrozole, Leuprolide, Levalbuterol, Levamisole hydrochloride, Levetiracetam, levocetirizine dihydrochloride, levodopa, Levofloxacin, levonorgestrel, Levothyroxine, levothyroxine sodium, Lidocaine, Linezolid, Lisdexamfetamine Dimesylate, Lisinopril, Lispro insulin, Lopinavir, Loratadine, lorazepam, Losartan potassium, maraviroc, Marinol, meclizine hydrochloride, Meloxicam, Memantine, Meropenem, metaxalone, metformin, Metformin Hydrochloride, methadone, methoxy polyethylene glycol-epoetin beta, Methylphenidate, Methylphenidate hydrochloride, Metoprolol, Metoprolol tartrate, metronidazole, Metronidazole, miglitol, Minocycline, Minocycline hydrochloride, mirtazepine, Modafinil, Mometasone, montelukast, Montelukast sodium, Morphine, Moxifloxacin, Mycophenolate mofetil, Naloxone, Naproxen sodium, natalizumab, Neostigmine bromide, Niacin, Nicotinamide, Nifedipine, Nifurtimox, nilotinib hydrochloride monohydrate, nitrofurantoin, Nortriptyline hydrochloride, nystatin, olanzapine, Olanzepine, Olmesartan, olmesartan medoxomil, olopatadine hydrochloride, Omalizumab, Omega-3 acid ethyl esters, Omeprazole, Ondansetron, Opioids, Opiod Antagonists, Orlistat, Oseltamivir, Oxaliplatin, Oxcarbazepine, Oxybytynin chloride, oxycodone hydrochloride, Paclitaxel, Palivizumab, Pantoprazole, paracetamol, Paroxetine, paroxetine hydrochloride, Pegylated interferon alfa-2a, Pemetrexed, Penicillamine, Penicillin V potassium, Phenformin, Phenyloin sodium, Pioglitazone, Piperacillin, Potassium chloride, Pramipexole, Pravastatin, Pravastatin sodium, prednisolone quetiapine fumerate, Pregabalin, Primaquine phosphate, Progesterone, Promethazine, Promethazine hydrochloride, Proponolol hydrochloride, Propoxyphene hydrochloride, pseudoephedrine, Pseudophedrine hydrochloride, Pyridostigmine bromide, Pyridoxine hydrochloride, Quetiapine, quetiapine fumarate, Quinapril hydrochloride, Rabeprazole, raloxifene, raltegravir, Ramipril, Ranitidine, Ranitidine hydrochloride, Recombinant factor VIII, retapamulin, Rimonabant, Risedronate, Risedronate sodium, risperidone, Ritonavir, rituximab, Rivastigmine, rivastigmine tartrate, Rizatriptan, Ropinirole, rosiglitazone, Rosiglitazone maleate, Rosuvastatin, Rotavirus vaccine, rotigotine, Salbutamol, Salbutamol sulfate, salmeterol, sapropterin dihydrochloride, Sertraline, sertraline hydrochloride, Sevelamer, Sevoflurane, Sildenafil, sildenafil citrate, simvastatin, Simvastatin, Sitagliptin, Sodium valproate, Solifenacin, Somatostatin, Somatropin, Stavudine, Sulfomethoxazole, Sumatriptan, Sumatriptan succinate, Tacrolimus, Tadalafil, tamoxifen citrate, Tamsulosin, tamsulosin hydrochloride, Tegaserod, Telmisartan, temazepam, Temozolomide, temsirolimus, Tenofovir, Terazosin Hydrochloride, Terbinafine, Teriparatide, testosterone, Tetracycline hydrochloride, Thalidomide, thymopentin, Timolol meleate, Tiotropium, tipranavir, Tolterodine, tolterodine tartrate, topiramate, topotecan, Tramadol, Tramodol hydrochloride, trastuzumab, trazodone hydrochloride, trimethoprim, Valaciclovir, Valacyclovir hydrochloride, Valproate semisodium, valsartan, Vancomycin, Vardenafil, Varenicline, venlafaxine, Venlafaxine hydrochloride, Verapamil Hydrochloride, vildagliptin, Voglibose, Voriconazole, Wafarin sodium acetylsalicylic acid, Zaleplon, Zidovudine, Ziprasidone, Zoledronate, Zolpidem, or pharmaceutically acceptable salts thereof; 16-alpha fluoroestradiol, 17-alpha dihydroequilenin, 17-alpha estradiol, 17-beta estradiol, 17-hydroxyprogesterone, 1-dodecpyrrolidinone, 22-oxacalcitriol, 3-isobutyl-gammabutyric acid, 6-fluoroursodeoxycholic acid, 7-methoxytacrine, Abacavir, Abacavir sulfate, Abamectin, abanoquil, abatacept, abecarnil, abiraterone, Ablukast, Ablukast Sodium, Acadesine, acamprosate, Acarbose, Acebutolol, Acecamide Hydrochloride, Aceclidine, aceclofenae, Acedapsone, Acedapsone, Aceglutamide Aluminum, Acemannan, Acetaminophen, Acetazolamide, Acetohexamide, Acetohydroxamic Acid, acetomepregenol, Acetophenazine Maleate, Acetosulfone Sodium, Acetylcholine Chloride, Acetylcysteine, acetyl-L-carnitine, acetylmethadol, Aciclovir, Acifran, acipimox, acitemate, Acitretin, Acivicin, Aclarubicin, aclatonium, Acodazole Hydrochloride, aconiazide, Acrisorcin, Acrivastine, Acronine, Actisomide, Actodigin, Acyclovir, acylfulvene, Adatanserin Hydrochloride, adafenoxate, Adalimumab, Adapalene, adatanserin, adecypenol, adecypenol, Adefovir, adelmidrol, ademetionine, Adenosine, Adinazolam, Adipheinine Hydrochloride, adiposin, Adozelesin, adrafinil, Adrenalone, Aiclometasone Dipropionate, airbutamine, alacepril, Alamecin, Alanine, Alaproclate, alaptide, Albendazole, albolabrin, Albuterol, Alclofenae, Alcloxa, aldecalmycin, Aldesleukin, Aldioxa, Aletamine Hydrochloride, Alendronate, Alendronate Sodium, alendronic acid, alentemol, Alentemol Hydrobromide, Aleuronium Chloride, Alexidine, alfacalcidol, Alfentanil Hydrochloride, alfuzosin, Algestone Acetonide, alglucerase, Aliflurane, alinastine, Alipamide, aliskiren, Allantoin, Allobarbital, Allopurinol, Alonimid, alosetron, Alosetron Hydrochloride, Alovudine, Alpertine, alpha-idosone, Alpidem, Alprazolam, Alprenolol Hydrochloride, Alprenoxime Hydrochloride, Alprostadil, Alrestatin Sodium, Altanserin Tartrate, Alteplase, Althiazide, Altretamine, altromycin B, Alverinc Citrate, alvimopan, Alvircept Sudotox, Amadinone Acetate, Amantadine Hydrochloride, ambamustine, Ambomycin, ambrisentan, Ambruticin, Ambuphylline, Ambuside, Amcinafal, Amcinonide, Amdinocillin, Amdinocillin Pivoxil, Amedalin Hydrochloride, amelometasone, Ameltolide, Amesergide, Ametantrone Acetate, amezinium metilsulfate, amfebutamone, Amfenac Sodium, Amfiutizole, Amicycline, Amidephrine Mesylate, amidox, Amifloxacin, amifostine, Amilcacin, Amiloride Hydrochloride, Aminacrine Hydrochloride, Aminobenzoate Potassium, Aminobenzoate Sodium, Aminocaproic Acid, Aminoglutethimide, Aminohippurate Sodium, aminolevulinic acid, Aminophylline, A minorex, Aminosalicylate sodium, Aminosalicylic acid, Amiodarone, Amiprilose Hydrochloride, Amiquinsin Hydrochloride, amisulpride, Amitraz, Amitriptyline Hydrochloride, Amlexanox, amlodipine, amlodipine besylate, Amobarbital Sodium, Amodiaquine, Amodiaquine Hydrochloride, Amorolfine, Amoxapine, Amoxicillin, Amphecloral, Amphetamine, Amphetamine Sulfate, Amphomycin, Amphoterin B, Ampicillin, ampiroxieam, Ampyzine Sulfate, Amquinate, Amrinone, amrubicin, Amsacrine, Amylase, amylin, amythiamicin, Anagestone Acetate, anagrelide, Anakinra, ananain, anaritide, Anaritide Acetate, Anastrozole, Anazolene Sodium, Ancrod, andrographolide, Androstenedione, Angiotensin Amide, Anidoxime, Anileridine, Anilopam Hydrochloride, Aniracetam, Anirolac, Anisotropine Methylbromide, Anistreplase, Anitrazafen, anordrin, antagonist D, antagonist G, antarelix, Antazoline Phosphate, Anthelmycin, Anthralin, Anthramyciantiandrogen, antiestrogen, antineoplaston, Antipyrine, antisense oligonucleotides, apadoline, apafant, Apalcillin Sodium, apaxifylline, Apazone, aphidicolin glycinate, Apixifylline, Apomorphine Hydrochloride, apraclonidine, Apraclonidine Hydrochloride, Apramycin, Aprindine, Aprindine Hydrochloride, aprosulate sodium, Aprotinin, Aptazapine Maleate, aptiganel, apurinic acid, apurinic acid, aranidipine, Aranotin, Arbaprostil, arbekicin, arbidol, Arbutamine Hydrochloride, Arclofenin, Ardeparin Sodium, argatroban, Arginine, Argipressin Tannate, Arildone, Aripiprazole, armodafinil, arotinolol, Arpinocid, Arteflene, Artilide Fumarate, asimadoline, aspalatone, Asparaginase, Aspartic Acid, Aspartocin, asperfuran, Aspirin, aspoxicillin, Asprelin, Astemizole, Astromicin Sulfate, asulacrine, atamestane, Atazanavir, Atenolol, atevirdine, Atipamezole, Atiprosin Maleate, Atolide, Atomoxetine, atorvastatin, Atorvastatin Calcium, Atosiban, Atovaquone, atpenin B, Atracurium Besylate, atrimustine, atrinositol, Atropine, Atropine sulfate, Auranofin, aureobasidin A, Aurothioglucose, Avilamycin, Avoparcin, Avridine, Axid, axinastatin 1, axinastatin 2, axinastatin 3, Azabon, Azacitidinie, Azaclorzine Hydrochloride, Azaconazole, azadirachtine, Azalanstat Dihydrochloride, Azaloxan Fumarate, Azanator Maleate, Azanidazole, Azaperone, Azaribine, Azaserine, azasetron, Azatadine Maleate, Azathioprine, Azathioprine Sodium, azatoxin, azatyrosine, azelaic acid, Azelastine, azelnidipine, Azepindole, Azetepa, azimilide, Azithromycin, Azlocillin, Azolimine, Azosemide, Azotomycin, Aztreonam, Azumolene Sodium, Bacampicillin Hydrochloride, baccatin III, Bacitracin, Baclofen, bacoside A, bacoside B, bactobolamine, balanol, balazipone, balhimycin, balofloxacin, balsalazide, Bambermycins, bambuterol, Bamethan Sulfate, Bamifylline Hydrochloride, Bamidazole, baohuoside 1, Barmastine, barnidipine, Basic, Basifungin, Batanopride Hydrochloride, batebulast, Batelapine Maleate, Batimastat, beau vericin, Becanthone Hydrochloride, becaplermin, becliconazole, Beclomethasone Dipropionate, befloxatone, Beinserazide, Belfosdil, Belladonna, Beloxamide, Bemesetron, Bemitradine, Bemoradan, Benapryzine Hydrochloride, Benazepril, Benazepril Hydrochloride, Benazeprilat, Bendacalol Mesylate, bendamustine hydrochloride, Bendazac, Bendroflumethiazide, benflumetol, benidipine, Benorterone, Benoxaprofen, Benoxaprofen, Benoxinate Hydrochloride, Benperidol, Bentazepam, Bentiromide, Benurestat, Benzbromarone, Benzepril hydrochloride, Benzethonium Chloride, Benzetimide Hydrochloride, Benzilonium Bromide, Benzindopyrine Hydrochloride, benzisoxazole, Benzocaine, benzochlorins, Benzoctamine Hydrochloride, Benzodepa, benzoidazoxan, Benzonatate, Benzoyl Peroxide, benzoylstaurosporine, Benzquinamide, Benzthiazide, benztropine, Benztropine Mesylate, Benzydamine Hydrochloride, Benzylpenicilloyl Polylysine, bepridil, Bepridil Hydrochloride, Beractant, Beraprost, Berefrine, berlafenone, bertosamil, Berythromycin, besipirdine, betaalethine, betaclamycin B, Betamethasone, betamipron, betaxolol, Betaxolol Hydrochloride, Bethanechol Chloride, Bethanidine Sulfate, betulinic acid, bevacizumab, bevantolol, Bevantolol Hydrochloride, Bezafibrate, Bialamicol Hydrochloride, Biapenem, Bicalutamide, Bicifadine Hydrochloride, Biclodil Hydrochloride, Bidisomide, bifemelane, Bifonazole, bimakalim, Bimatoprost, bimithil, Bindarit, Biniramycin, binospirone, bioxalomycin, Bipenamol Hydrochloride, Biperiden, Biphenamine Hydrochloride, biriperone, bisantrene, bisaramil, bisaziridinylspermine, bis-benzimidzole A, bis-benzimidazole B, bisnafide, Bisobrin Lactate, Bisoprolol, Bisoprolol fumarate, Bispyrithione Magsulfex, bistramide D, bistramide K, bistratene A, Bithionolate Sodium, Bitolterol Mesylate, Bivalirudin, Bizelesin, Bleomycin Sulfate, boldine, Bolandiol Dipropionate, Bolasterone, Boldenone Undecylenate, Bolenol, Bolmantalate, bopindolol, Bosentan, Botulin toxin, Boxidine, brefeldin, breflate, Brequinar Sodium, Bretazenil, Bretylium Tosylate, Brifentanil Hydrochloride, brimonidine, Brinolase, Brocresine, Brocrinat, Brofoxine, Bromadoline Maleate, Bromazepam, Bromchlorenone, Bromelain, bromfenac, Brominidione, Bromocriptine, Bromodiphenhydramine Hydrochloride, Bromoxanide, Bromperidol, Bromperidol Decanoate, Brompheniramine Maleate, Broperamole, Bropirimine, Brotizolam, Bucamide Maleate, bucindolol, Buclizine Hydrochloride, Bucromarone, Budesonide, budipine, budotitane, Buformin, Bumetanide, Bunaprolast, bunazosin, Bunolol Hydrochloride, Bupicomide, Bupivacaine Hydrochloride, Buprenorphine, Buprenorphine Hydrochloride, Bupropion, bupropion hydrobromide, Bupropion Hydrochloride, Buramate, Buserelin Acetate, Buspirone Hydrochloride, Busulfan, Butabarbital, Butacetin, Butaclamol Hydrochloride, Butalbital, Butamben, Butamirate Citrate, Butaperazine, Butaprost, Butedronate Tetrasodium, butenafine, Buterizine, buthioninc sulfoximine, Butikacin, Butilfenin, Butirosin Sulfate, Butixirate, butixocort propionate, Butoconazole Nitrate, Butonate, Butopamine, Butoprozine Hydrochloride, Butorphanol, Butoxamine Hydrochloride, Butriptyline Hydrochloride, Cabergoline, Cactinomycin, Cadexomer Iodine, Caffeine, calanolide A, Calcifediol, Calcipotriene, calcipotriol, Calcitonin, Calcitriol, Calcium Undecylenate, calphostin C, Calusterone, Cambendazole, Cammonam Sodium, camonagrel, canary pox IL-2, candesartan, candesartan cilexetil, Candicidin, candoxatril, candoxatrilat, Caniglibose, Canrenoate Potassium, Canrenone, capecitabine, Capobenate Sodium, Capobenic Acid, Capreomycin Sulfate, capromab, capsaicin, Captopril, Capuride, Car bocysteine, Caracemide, Carbachol, Carbadox, Carbamazepine, Carbamide Peroxide, Carbantel Lauryl Sulfate, Carbaspirin Calcium, Carbazeran, carbazomycin C, Carbenicillin Potassium, Carbenoxolone Sodium, Carbetimer, carbetocin, Carbidopa, Carbidopa-Levodopa, Carbinoxamine Maleate, Carbiphene Hydrochloride, Carbocloral, Carbol-Fuchsin, Carboplatin, Carboprost, carbovir, carboxamide-amino-triazo-1e, carboxyamidotriazole, carboxymethylated beta-1,3-glucan, Carbuterol Hydrochloride, CaRest M3, Carfentanil Citrate, Carisoprodol, Carmantadine, Carmustine, CARN 700, Carnidazole, Caroxazone, carperitide, Carphenazine Maleate, Carprofen, Carsatrin Succinate, Cartazolate, carteolol, Carteolol Hydrochloride, Carubicin Hydrochloride, carvedilol, carvotroline, Carvotroline Hydrochloride, carzelesin, Caspofungin, castanospermine, caurumonam, cebaracetam, cecropin B, Cedefingol, Cefaclor, Cefadroxil, Cefamandole, Cefaparole, Cefatrizine, Cefazaflur Sodium, Cefazolin, cefcapene pivoxil, cefdaloxime pentexil tosilate, Cefdinir, cefditoren pivoxil, Cefepime, cefetamet, Cefetecol, cefixime, cefluprenam, Cefinenoxime Hydrochloride, Cefinetazole, cefminlox, cefodizime, Cefonicid Sodium, Cefoperazone, Cefoperazone Sodium, Ceforanide, cefoselis, Cefotaxime Sodium, Cefotetan, cefotiam, Cefoxitin, cefozopran, cefpimizole, Cefpiramide, cefpirome, cefpodoxime proxetil, cefprozil, Cefroxadine, cefsulodin, Ceftazidime, cefteram, ceftibuten, Ceftizoxime Sodium, ceftriaxooe, Cefuroxime, celastrol, Celecoxib, celikalim, celiprolol, cepacidiine A, Cephacetrile Sodium, Cephalexin, Cephaloglycin, Cephaloridine, Cephalothin Sodium, Cephapirin Sodium, Cephradine, cericlamine, cerivastatin, Ceruletide, Ceronapril, Certolizumab Pegol, certoparin sodium, Cetaben Sodium, Cetalkonium Chloride, Cetamolol Hydrochloride, Cethuperazone, cetiedil, cetirizine, Cetophenicol, Cetraxate Hydrochloride, Cetrizine hydrochloride, cetrorelix, Cetuximab, Cetylpyridinium Chloride, Chenodiol, Chlophedianol Hydrochloride, Chloral Betaine, Chlorambucil, Chloramphenicol, Chlordantoin, Chlordiazepoxide, Chlorhexidine Gluconate, chlorins, Chlormadinone Acetate, chloroorienticin A, Chloroprocaine Hydrochloride, Chloropropamide, Chloroquine, chloroquinoxaline sulfonamide, Chlorothiazide, Chlorotrianisene, Chloroxine, Chloroxylenol, Chlorpheniramine Maleate, Chlorphenesin Carbamate, Chlorpheniramine maleate, Chlorpromazine, Chlorpromazine hydrochloride, Chlorpropamide, Chlorprothixene, Chlortetracycline Bisulfate, Chlorthalidone, Chlorzoxazone, Cholestyramine Resin, Chromonar Hydrochloride, cibenzoline, cicaprost, Ciclafrine Hydrochloride, Ciclazindol, ciclesonide, cicletanine, Ciclopirox, Cicloprofen, cicloprolol, Cidofovir, Cidoxepin Hydrochloride, Cifenline, Ciglitazone, Ciladopa Hydrochloride, cilansetron, Cilastatin, Cilastatin Sodium, Cilazapril, cilnidipine, Cilobamine Mesylate, cilobradine, Cilofungin, cilostazol, Cimaterol, Cimetidine, cimetropium bromide, Cinacalcet, Cinalukast, Cinanserin Hydrochloride, Cinepazet Maleate, Cinflumide, Cingestol, cinitapride, Cinnamedrine, Cinnarizine, cinolazepam, Cinoxacin, Cinperene, Cinromide, Cintazone, Cintriamide, Cioteronel, Cipamfylline, Ciprefadol Succinate, Ciprocinonide, Ciprofibrate, Ciprofloxacin, ciprostene, Ciramadol, Cirolemycin, Cisplatin, cisapride, cisatracurium besilate, Cisconazole, cis-porphyrin, cistinexine, citalopram, citalopram hydrobromide, Citenamide, citicoline, citreamicin alpha, cladribine, Clamoxyquin Hydrochloride, Clarithromycin, clausenamide, Clavulanate Potassium, Clazolam, Clazolimine, clebopride, Clemastine, Clentiazem Maleate, Clidinium Bromide, clinafloxacin, Clindamycin, clindamycin hydrochloride, Clioquinol, Clioxanide, Cliprofen, clobazam, Clobetasol Propionate, Clobetasone Butyrate, Clocortolone Acetate, Clodanolene, Clodazon Hydrochloride, clodronic acid, Clofazimine, Clofibrate, Clofilium Phosphate, Cloge stone Acetate, Clomacran Phosphate, Clomegestone Acetate, Clometherone, clomethiazole, clomifeneanalogues, Clominorex, Clomiphene, Clomipramine Hydrochloride, Clonazepam, Clonidine, Clonidine hydrochloride, Clonitrate, Clonixeril, Clonixin, Clopamide, Clopenthixol, Cloperidone Hydrochloride, clopidogrel, Clopidogrel bisulfate, Clopimozide, Clopipazan Mesylate, Clopirac, Cloprednol, Cloprostenol Sodium, Clorazepate Dipotassium, Clorethate, Clorexolone, Cloroperone Hydrochloride, Clorprenaline Hydrochloride, Clorsulon, Clortemine Hydrochloride, Closantel, Closiramine Aceturate, Clothiapine, Clothixamide Maleate Cloticasone Propionate, Clotrimazole, Cloxacillin Benzathine, Cloxacillin Sodium, Cloxyquin, Clozapine, Co-Amoxiclav, Cocaine, Coccidioidin, Codeine, Codeine phosphate, Codoxime, Colchicine, Colesevelam, colestimide, Colestipol Hydrochloride, Colestolone, Colforsin, Colfosceril Palmitate, Colistimethate Sodium, Colistin Sulfate, collismycin A, collismycin B, Colterol Mesylate, combretastatin A4, complestatin, conagenin, Conorphone Hydrochloride, contignasterol, contortrostatin, Cormethasone Acetate, Corticorelin Ovine Tnflutate, Corticotropin, Cortisone Acetate, Cortivazol, Cortodoxone, cosalane, costatolide, Cosyntropin, cotinine, Coumadin, Coumermycin, crambescidin, Crilvastatin, crisnatol, Cromitrile Sodium, Cromolyn Sodium, Crotamiton, cryptophycin, cucumariosid, Cuprimyxin, curacin A, curdlan sulfate, curiosin, Cyclacillin, Cyclazocine, cyclazosin, Cyclindole, Cycliramine Maleate, Cyclizine, Cyclobendazole, cyclobenzaprine, cyclobenzaprine hydrochloride, cyclobut A, cyclobut G, cyclocapron, Cycloguanil Pamoate, Cycloheximide, cyclopentanthraquinones, Cyclopenthiazide, Cyclopentolate Hydrochloride, Cyclophenazine Hydrochloride, Cyclophosphamide, cycloplatam, Cyclopropane, Cycloserine, cyclosin, Cyclosporine, cyclothialidine, Cyclothiazide, cyclothiazomycin, Cyheptamide, cypemycin, Cyponamine Hydrochloride, Cyprazepam, Cyproheptadine Hydrochloride, Cyprolidol Hydrochloride, cyproterone, Cyproximide, Cysteamine, Cysteine Hydrochloride, Cystine, Cytarabine, Cytarabine Hydrochloride, cytarabine ocfosfate, cytochalasin B, cytostatin, Dacarbazine, dacliximab, dactimicin, Dactinomycin, daidzein, Daledalin Tosylate, dalfopristin, Dalteparin Sodium, Daltroban, Dalvastatin, danaparoid, Danazol, Dantrolene, daphlnodorin A, dapiprazole, dapitant, Dapoxetine Hydrochloride, Dapsone, Daptomycin, darbepoetin alfa, Darglitazone Sodium, darifenacin, darlucin A, Darodipine, darsidomine, Daunorubicin Hydrochloride, Dazadrol Maleate, Dazepinil Hydrochloride, Dazmegrel, Dazopride Fumarate, Dazoxiben Hydrochloride, DCRM 197 protein, Debrisoquin Sulfate, Decitabine, deferiprone, deflazacort, Dehydrocholic Acid, dehydrodidemnin B, Dehydroepiandrosterone, delapril, Delapril Hydrochloride, Delavirdine Mesylate, delequamine, delfaprazine, Delmadinone Acetate, delmopinol, delphinidin, Demecarium Bromide, Demeclocycline, Demecycline, Demoxepam, Denofungin, deoxypyridinoline, Depakote, deprodone, Deprostil, depsidomycin, deramciclane, dermatan sulfate, Desciclovir, Descinolone Acetonide, Desfurane, Desipramine Hydrochloride, desirudin, Deslanoside, Desloratadine, deslorelin, desmopressin, Desmopressin sulfate, desogestrel, Desonide, Desoximetasone, desoxoamiodarone, Desoxy-corticosterone Acetate, detajmium bitartrate, Deterenol Hydrochloride, Detirelix Acetate, Devazepide, Dexamethasone, Dexamisole, Dexbrompheniramine Maleate, Dexchlorpheniramine Maleate, Dexclamol Hydrochloride, Dexetimide, Dexfenfluramine Hydrochloride, dexifosfamide, Deximafen, dexketoprofen, dexloxiglumide, Dexmedetomidine, Dexormaplatin, Dexoxadrol Hydrochloride, Dexpanthenol, Dexpemedolac, Dexpropranolol Hydrochloride, Dexrazoxane, dexsotalol, dextrin 2-sulphate, Dextroamphetamine, Dextromethorphan, Dextrorphan Hydrochloride, Dextrothyroxine Sodium, dexverapamil, Dezaguanine, dezinamide, dezocine, Diacetolol Hydrochloride, Diamocaine Cyclamate, Diapamide, Diatrizoate Meglumine, Diatrizoic Acid, Diaveridine, Diazepam, Diaziquone, Diazoxide, Dibenzepin Hydrochloride, Dibenzothiophene, Dibucaine, Dichliorvos, Dichloralphenazone, Dichlorphenamide, Dicirenone, Diclofenac, Diclofenac Sodium, Dicloxacillin, dicranin, Dicumarol, Dicyclomine Hydrochloride, Didanosine, didemnin B, didox, Dienestrol, dienogest, Diethylcarbamazine Citrate, diethylhomospermine, diethylnorspermine, Diethylpropion Hydrochloride, Diethylstilbestrol, Difenoximide Hydrochloride, Difenoxin, Diflorasone Diacetate, Difloxacin Hydrochloride, Difluanine Hydrochloride, Diflucortolone, Diflumidone Sodium, Diflunisal, Difluprednate, Diftalone, Digitalis, Digitoxin, Digoxin, Dihexyverine Hydrochloride, dihydrexidine, dihydro-5-azacytidine, Dihydrocodeine Bitartrate, Dihydroergotamine Mesylate, Dihydroestosterone, Dihydrostreptomycin Sulfate, Dihydrotachysterol, Dilantin, Dilevalol Hydrochloride, Diltiazem Hydrochloride, Dimefadane, Dimefline Hydrochloride, Dimenhydrinate, Dimercaprol, Dimethadione, Dimethindene Maleate, Dimethisterone, Dimethyl Sulfoxide, dimethylhomospermine, dimethylprostaglandin A1, dimiracetam, Dimoxamine Hydrochloride, Dinoprost, Dinoprostone, Dioxadrol Hydrochloride, dioxamycin, diphenhydramine, Diphenhydramine Citrate, Diphenidol, Diphenoxylate Hydrochloride, diphenylspiromustine, Dipivefin Hydrochloride, Dipivefrin, dipliencyprone, diprafenone, dipropylnorspermine, Dipyridamole, Dipyrithione, Dipyrone, dirithromycin, discodermolide, Disobutamide, Disofenin, Disopyramide, Disoxaril, disulfuram, Ditekiren, Divalproex Sodium, Dizocilpine Maleate, DL-methionine, Dobutamine, docarpamine, Docebenone, Docetaxel, Doconazole, docosanol, dofetilide, dolasetron, Donepezil, doripenem, Dorzolamide, Doxazosin, doxazosin mesylate, doxycydine, Drospirenone, Duloxetine, Dutasteride, Ebastine, ebiratide, ebrotidine, ebselen, ecabapide, ecabet, ecadotril, ecdisteron, echicetin, echistatin, Echothiophate Iodide, Eclanamine Maleate, Eclazolast, ecomustine, Econazole, ecteinascidin 722, eculizumab, edaravone, Edatrexate, edelfosine, Edifolone Acetate, edobacomab, Edoxudine, edrecolomab, Edrophonium Chloride, edroxyprogesteone Acetate, Efavirenz, efegatran, eflornithine, efonidipine, egualcen, Elantrine, eleatonin, elemene, eletriptan, elgodipine, eliprodil, Elsamitrucin, eltenae, Elucaine, emailcalim, emedastine, Emetine Hydrochloride, emiglitate, Emilium Tosylate, emitefur, emoctakin, Emtricitabine, Enadoline Hydrochloride, Enailciren, enalapril, enalapril maleate, enazadrem, Encyprate, Endralazine Mesylate, Endrysone, Enflurane, englitazone, Enilconazole, Enisoprost, Enlimomab, Enloplatin, Enofelast, Enolicam Sodium, Enoxacin, enoxacin, enoxaparin sodium, Enoxaparin Sodium, Enoximone, Enpiroline Phosphate, Enprofylline, Enpromate, entacapone, enterostatin, Enviradene, Enviroxime, Ephedrine, Epicillin, Epimestrol, Epinephrine, Epinephryl Borate, Epipropidine, Epirizole, epirubicin, Epitetracycline Hydrochloride, Epithiazide, Epoetin Alfa, Epoetin Beta, Epoprostenol, Epoprostenol Sodium, epoxymexrenone, episteride, Eprosartan, eptastigmine, equilenin, Equilin, Erbulozole, erdosteine, Ergoloid Mesylates, Ergonovine Maleate, Ergotamine Tartrate, Erlotinib, ersentilide, Ersofermin, erythritol, Erythrityl Tetranitrate, Erythromycin, Erythropoetin, Escitalopram, Esmolol Hydrochloride, esomeprazole, Esorubicin Hydrochloride, Esproquin Hydrochloride, Estazolam, Estradiol, Estramustine, Estrazinol Hydrobromide, Estriol, Estrofurate, Estrogen, Estrone, Estropipate, esuprone, Eszopiclone, Etafedrine Hydrochloride, etanercept, Etanidazole, etanterol, Etarotene, Etazolate Hydrochloride, Eterobarb, ethacizin, Ethacrynate Sodium, Ethacrynic Acid, Ethambutol Hydrochloride, Ethamivan, Ethanolamine Oleate, Ethehlorvynol, Ethembutol hydrochloride, Ethinyl estradiol, Ethiodized Oil, Ethionamide, Ethonam Nitrate, Ethopropazine Hydrochloride, Ethosuximide, Ethosuximide, Ethotoin, Ethoxazene Hydrochloride, Ethybenztropine, Ethyl Chloride, Ethyl Dibunate, Ethylestrenol, Ethyndiol, Ethynerone, ethynl estradiol, Ethynodiol Diacetate, Etibendazole, Etidocaine, Etidronate Disodium, Etidronic Acid, Etifenin, Etintidine Hydrochloride, etizolam, Etodolac, Etofenamate, Etoformin Hydrochloride, Etomidate, Etonogestrel, Etoperidone Hydrochloride, Etoposide, Etoprine, etoricoxib, Etoxadrol Hydrochloride, Etozolin, etrabamine, etravirine, Etretinate, Etryptamine Acetate, Eucatropine Hydrochloride, Eugenol, Euprocin Hydrochloride, eveminomicin, Exametazime, examorelin, Exaprolol Hydrochloride, exemestane, Exenatide, Ezetimibe, Ezetimibe, Factor VII, fadrozole, faeriefungin, Famciclovir, Famotidine, Fampridine, fantofarone, Fantridone Hydrochloride, faropenem, fasidotril, fasudil, fazarabine, fedotozine, Felbamate, felbamate, Felbinac, Felodipine, Felypressin, Fenalamide, Fenamole, Fenbendazole, Fenbufen, Fencibutirol, Fenclofenac, Fenclonine, Fenclorac, Fendosal, Fenestrel, Fenethylline Hydrochloride, Fenfluramine Hydrochloride, Fengabine, Fenimide, Fenisorex, Fenmetozole Hydrochloride, Fenmetramide, Fenobam, Fenoctimine Sulfate, Fenofibrate, fenoldopam, Fenoprofen, Fenoterol, Fenpipalone, Fenprinast Hydrochloride, Fenprostalene, Fenquizone, fenretinide, fenspiride, fentanyl, Fentanyl Citrate, Fentiazac, Fenticlor, fenticonazole, Fenyripol Hydrochloride, fepradinol, ferpifosate sodium, ferristene, ferrixan, Ferrous Sulfate, Ferumoxides, ferumoxsil, Fetoxylate Hydrochloride, Fexofenadine, fexofenadine hydrochloride, Fezolamine Fumarate, Fiacitabine, Fialuridine, fibmoxef, Fibrinogen, Filgrastim, Filipin, Finasteride, fiorfenicol, fiorifenine, fiosatidil, fiumecinol, fiunarizine, fiuparoxan, fiupirtine, fiurithromycin, fiutrimazole, fiuvastatin, fiuvoxamine, Flavodilol Maleate, flavopiridol, Flavoxate Hydrochloride, Flazalone, flecamide, flerobuterol, Fleroxacin, flesinoxan, Flestolol Sulfate, Fletazepam, flezelastine, flobufen, Floctafenine, Flordipine, Flosequinan, Floxacillin, Floxuridine, fluasterone, Fluazacort, Flubanilate Hydrochloride, Flubendazole, Flucindole, Flucloronide, Fluconazole, Flucytosine, Fludalanine, Fludarabine Phosphate, Fludazonium Chloride, Fludeoxyglucose, Fludorex, Fludrocortisone Acetate, Flufenamic Acid, Flufenisal, Flumazenil, Flumequine, Flumeridone, Flumethasone, Flumetramide, Flumezapine, Fluminorex, Flumizole, Flumoxonide, Flunidazole, Flunisolide, Flunitrazepam, Flunixin, fluocalcitriol, Fluocinolone Acetonide, Fluocinonide, Fluocortin Butyl, Fluocortolone, Fluorescein, fluorodaunorunicin hydrochloride, Fluorodopa, Fluorometholone, Fluorouracil, Fluotracen Hydrochloride, Fluoxetine, Fluoxetine hydrochloride, Fluoxymesterone, Fluperamide, Fluperolone Acetate, Fluphenazine Decanoate, Fluprednisolone, Fluproquazone, Fluprostenol Sodium, Fluquazone, Fluradoline Hydrochloride, Flurandrenolide, Flurazepam Hydrochloride, Flurbiprofen, Fluretofen, Fluorocitrabine, Fluorofamide, Fluorogestone Acetate, Fluorothyl, Fluoroxene, Fluspiperone, Fluspirilene, Fluticasone, Fluticasone Propionate, Flutroline, Fluvastatin, Fluvastatin Sodium, Fluzinamide, Folic Acid, Follicle regulatory protein, Folliculostatin, Follitropin alfa, Follitropin beta, Fomepizole, Fonazine Mesylate, forasartan, forfenimex, forfenirmex, formestane, Formocortal, formoterol, Fosarilate, Fosazepam, Foscarnet Sodium, fosfomycin, Fosfonet Sodium, fosinopril, Fosinopril sodium, Fosinoprilat, fosphenyloin, Fosquidone, Fostedil, fostriecin, fotemustine, Fuchsin, Fumoxicillin, Fungimycin, Furaprofen, Furazolidone, Furazolium Chloride, Furegrelate Sodium, Furobufen, Furodazole, Furosemide, Fusidate Sodium, Fusidic Acid, Gabapentin, Gadobenate Dimeglumine, gadobenic acid, gadobutrol, Gadodiamide, gadolinium texaphyrin, Gadopentetate Dimegiumine, gadoteric acid, Gadoteridol, Gadoversetamide, galantamine, galdansetron, Galdansetron Hydrochloride, Gallamine Triethiodide, gallium nitrate, gallopamil, galocitabine, Gamfexine, gamolenic acid, Ganciclovir, ganirelix, Gemcadiol, Gemcitabine, Gemeprost, Gemfibrozil, Gentamicin Sulfate, Gentian Violet, gepirone, Gestaclone, Gestodene, Gestonorone Caproate, Gestrinone, Gevotroline Hydrochloride, girisopam, glargine insulin, glaspimod, Glatiramer, glaucocalyxin A, Glemanserin, Gliamilide, Glibornuride, Glicetanile Sodium, Glifiumide, Glimepiride, Glipizide, Gloximonam, Glucagon, glutapyrone, Glutethimide, Glyburide, glycopine, glycopril, Glycopyrrolate, Glyhexamide, Glymidine Sodium, Glyoctamide, Glyparamide, Gold Au-198, Gonadoctrinins, Gonadorelin, Gonadotropins, Goserelin, Gramicidin, Granisetron, grepafloxacin, Griseofulvin, Guaiapate, Guaithylline, Guanabenz, Guanabenz Acetate, Guanadrel Sulfate, Guancydine, Guanethidine Monosulfate, Guanfacine Hydrochloride, Guanisoquin Sulfate, Guanoclor Sulfate, Guanoctine Hydrochloride, Guanoxabenz, Guanoxan Sulfate, Guanoxyfen Sulfate, Gusperimus Trihydrochloride, Halazepam, Halcinonide, halichondrin B, Halobetasol Propionate, halofantrine, Halofantrine Hydrochloride, Halofenate, Halofuginone Hydrobromide, halomon, Halopemide, Haloperidol, halopredone, Haloprogesterone, Haloprogin, Halothane, Halquinols, Hamycin, hatomamicin, hatomarubigin A, hatomarubigin B, hatomarubigin C, hatomarubigin D, Heparin Sodium, hepsulfam, heregulin, Hetacillin, Heterooium Bromide, Hexachlorophene Hydrogen Peroxide, Hexafluorenium Bromide, hexamethylene bisacetamide, Hexedine, Hexobendine, Hexoprenaline Sulfate, Hexylresorcinol, Histamine Phosphate, Histidine, Histoplasmin, Histrelin, histrelin acetate, Homatropine Hydrobromide, Hoquizil Hydrochloride, Human chorionic gonadotropin, Human growth hormone, Hycanthone, Hydralazine Hydrochloride, Hydralazine Polistirex, Hydrochlorothiazide, Hydrocodone Bitartrate, Hydrocortisone, Hydroflumethiazide, Hydromorphone Hydrochloride, Hydroxyamphetamine Hydrobromide, Hydroxychloroquine Sulfate, Hydroxyphenamate, Hydroxyprogesterone Caproate, Hydroxyurea, Hydroxyzine Hydrochloride, Hymecromone, Hyoscyamine, hypericin, Ibafloxacin, Ibandronate, ibogaine, Ibopam, ibudilast, Ibufenac, Ibuprofen, Ibutilide Fumarate, Icatibant Acetate, Ichthammol, Icotidine, idarubicin, idoxifene, Idoxuridine, idramantone, Ifetroban, Ifosfamide, Ilepeimide, illimaquinone, ilmofosin, ilomastat, Ilonidap, iloperidone, iloprost, Imafen Hydrochloride, Imatinib, Imazodan Hydrochloride, imidapril, imidazenil, imidazoacridone, Imidecyl Iodine, Imidocarb Hydrochloride, Imidoline Hydrochloride, Imidurea, Imiglucerase, Imiloxan Hydrochloride, Imipenem, Imipramine Hydrochloride, imiquimod, Impromidine Hydrochloride, Indacrinone, Indapamide, Indecamide Hydrochloride, Indeloxazine Hydrochloride, Indigotindisulfonate Sodium, indinavir, Indinavir sulfate, Indocyanine Green, Indolapril Hydrochloride, Indolidan, indometacin, Indomethacin Sodium, Indoprofen, indoramin, Indorenate Hydrochloride, Indoxole, Indriline Hydrochloride, infliximab, inocoterone, inogatran, inolimomab, Inositol Niacinate, Insulin, Interferon beta-1a, Intrazole, Intriptyline Hydrochloride, iobenguane, Iobenzamic Acid, iobitridol, Iodine, iodoamiloride, iododoxorubicin, iofratol, iomeprol, iopentol, iopromide, iopyrol, iotriside, ioxilan, ipazilide, ipenoxazone, ipidacrine, Ipodate Calcium, ipomeanol, Ipratropium, Ipratropium Bromide, ipriflavone, Iprindole, Iprofenin, Ipronidazole, Iproplatin, Iproxamine Hydrochloride, ipsapirone, irbesartan, irinotecan, irloxacin, iroplact, irsogladin, Irtemazole, isalsteine, Isamoxole, isbogrel, Isepamicin, isobengazole, Isobutamben, Isocarboxazid, Isoconazole, Isoetharine, isofloxythepin, Isoflupredone Acetate, Isoflurane, Isofluorophate, isohomohalicondrin B, Isoleucine, Isomazole Hydrochloride, Isomylamine Hydrochloride, Isoniazid, Isopropamide Iodide, Isopropyl Alcohol, isopropyl unoprostone, Isoproterenol Hydrochloride, Isosorbide, Isosorbide Mononitrate, Isotiquimide, Isotretinoin, Isoxepac, Isoxicam, Isoxsuprine Hydrochloride, isradipine, isgitameline, itasetron, Itazigrel, itopride, Itraconazole, Ivermectin, ixabepilone, jasplakinolide, Jemefloxacin, Jesopitron, Josamycin, kahalalide F, Kalafungin, Kanamycin Sulfate, ketamine, Ketanserin, Ketazocine, Ketazolam, Kethoxal, Ketipramine Fumarate, Ketoconazole, Ketoprofen, Ketorfanol, ketorolac, Ketotifen Fumarate, Kitasamycin, Labetalol Hydrochloride, Lacidipine, lacidipine, lactitol, lactivicin, Lactobionate, laennec, lafutidine, 1-alphahydroxyvitamin D2, lamellarin-N triacetate, lamifiban, Lamivudine, Lamotrigine, lanoconazole, Lanoxin, lanperisone, lanreotide, lanreotide acetate, Lansoprazole, lapatinib, laropiprant, latanoprost, lateritin, laurocapram, Lauryl Isoquinolinium Bromide, Lavoltidine Succinate, lazabemide, Lecimibide, leinamycin, lemildipine, leminoprazole, lenercept, Leniquinsin, lenograstim, Lenperone, lentinan sulfate, leptin, leptolstatin, lercanidipine, Lergotrile, lerisetron, Letimide Hydrochloride, letrazuril, letrozole, Leucine, leucomyzin, leuprolide, Leuprolide Acetate, leuprorelin, Levalbuterol, Levamfetamine Succinate, levamisole, Levdobutamine Lactobionate, Leveromakalim, levetiracetam, Leveycloserine, levobetaxolol, levobunolol, levobupivacaine, levocabastine, levocarnitine, levocetirizine, levocetirizine dihydrochloride, Levodopa, levodropropizine, levofloxacin, Levofuraltadone, Levoleucovorin Calcium, Levomethadyl Acetate, Levomethadyl Acetate Hydrochloride, levomoprolol, Levonantradol Hydrochloride, Levonordefrin, Levonorgestrel, Levopropoxyphene Napsylate, Levopropylcillin Potassium, levormeloxifene, Levorphanol Tartrate, levosimendan, levosulpiride, Levothyroxine, Levothyroxine Sodium, Levoxadrol Hydrochloride, Lexipafant, Lexithromycin, liarozole, Libenzapril, Lidamidine Hydrochloride, Lidocaine, Lidofenin, Lidoflazine, Lifarizin, Lifibrate, Lifibrol, Linarotene, Lincomycin, Linezolid, Linogliride, Linopirdine, linotroban, linsidomine, lintitript, lintopride, Liothyronine 1-125, liothyronine sodium, Liotrix, lirexapride, Lisdexamfetamine Dimesylate, lisinopril, Lispro insulin, lissoclinamide, Lixazinone Sulfate, lobaplatin, Lobenzarit Sodium, Lobucavir, locarmate Meglumine, locarmic Acid, locetamic Acid, lodamide, Lodelaben, lodipamide Meglumine, lodixanol, Iodoantipyrine I-131, Iodocholesterol I-131, Iodohippurate Sodium I-131, Iodopyracet I-125, Iodoquinol, Iodoxamate Meglumine, lodoxamide, Iodoxamic Acid, Lofemizole Hydrochloride, Lofentanil Oxalate, Lofepramine Hydrochloride, lofetamine Hydrochloride I-123, Lofexidine Hydrochloride, loglicic Acid, loglucol, loglucomide, loglycamic Acid, logulamide, lohexyl, lombricine, Lomefloxacin, lomerizine, lomethin I-125, Lometraline Hydrochloride, lometrexol, Lomofungin, Lomoxicam, Lomustine, Lonapalene, lonazolac, lonidamine, lopamidol, lopanoic Acid, Loperamide Hydrochloride, lophendylate, Lopinavir, loprocemic Acid, lopronic Acid, lopydol, lopydone, loracarbef, Lorajmine Hydrochloride, loratadine, Lorazepam, Lorbamate, Lorcamide Hydrochloride, Loreclezole, Loreinadol, lorglumide, Lormetazepam, Lornoxicam, lornoxicam, Lortalamine, Lorzafone, losartan, Losartan potassium, losefamic Acid, loseric Acid, losigamone, losoxantrone, losulamide Meglumine, Losulazine Hydrochloride, losumetic Acid, lotasul, loteprednol, lotetric Acid, lothalamate Sodium, lothalamic Acid, lotrolan, lotroxic Acid, lovastatin, loversol, loviride, loxagiate Sodium, loxaglate Meglumine, loxaglic Acid, Loxapine, Loxoribine, loxotrizoic Acid, lubeluzole, Lucanthone Hydrochloride, Lufironil, Lurosetron Mesylate, lurtotecan, lutetium, Lutrelin Acetate, luzindole, Lyapolate Sodium, Lycetamine, lydicamycin, Lydimycin, Lynestrenol, Lypressin, Lysine, lysofylline, lysostaphin, Maduramicin, Mafenide, magainin 2 amide, Magnesium Salicylate, Magnesium Sulfate, magnolol, maitansine, Malethamer, mallotoaponin, mallotochromene, Malotilate, malotilate, mangafodipir, manidipine, maniwamycin A, Mannitol, mannostatin A, manumycin E, manumycin F, mapinastine, Maprotiline, maraviroc, marimastat, Marinol, Masoprocol, maspin, massetolide, Maytansine, Mazapertine Succiniate, Mazindol, Mebendazole, Mebeverine Hydrochloride, Mebrofenin, Mebutamate, Mecamylamine Hydrochloride, Mechlorethamine Hydrochloride, meclizine hydrochloride, Meclocycline, Meclofenamate Sodium, Mecloqualone, Meclorisone Dibutyrate, Medazepam Hydrochloride, Medorinone, Medrogestone, Medroxalol, Medroxyprogesterone, Medrysone, Meelizine Hydrochloride, Mefenamic Acid, Mefenidil, Mefenorex Hydrochloride, Mefexamide, Mefloquine Hydrochloride, Mefruside, Megalomicin Potassium Phosphate, Megestrol Acetate, Meglumine, Meglutol, Melengestrol Acetate, Meloxicam, Melphalan, Memantine, Memotine Hydrochloride, Menabitan Hydrochloride, Menoctone, menogaril, Menotropins, Meobentine Sulfate, Mepartricin, Mepenzolate Bromide, Meperidine Hydrochloride, Mephentermine Sulfate, Mephenyloin, Mephobarbital, Mepivacaine Hydrochloride, Meprobamate, Meptazinol Hydrochloride, Mequidox, Meralein Sodium, merbarone, Mercaptopurine, Mercufenol Chloride, Merisoprol, Meropenem, Mesalamine, Meseclazone, Mesoridazine, Mesterolone, Mestranol, Mesuprine Hydrochloride, Metalol Hydrochloride, Metaproterenol Polistirex, Metaraminol Bitartrate, Metaxalone, Meteneprost, meterelin, Metformin, Methacholine Chloride, Methacycline, methadone, Methadyl Acetate, Methalthiazide, Methamphetamine Hydrochloride, Methaqualone, Methazolamide, Methdilazine, Methenamine, Methenolone Acetate, Methetoin, Methicillin Sodium, Methimazole, methioninase, Methionine, Methisazone, Methixene Hydrochloride, Methocarbamol, Methohexital Sodium, Methopholine, Methotrexate, Methotrimeprazine, methoxatone, methoxy polyethylene glycol-epoetin beta, Methoxyflurane, Methsuximide, Methyclothiazide, Methyl Palmoxirate, Methylatropine Nitrate, Methylbenzethonium Chloride, Methyldopa, Methyldopate Hydrochloride, Methylene Blue, Methylergonovine Maleate, methylhistamine, methylinosine monophosphate, Methylphenidate, Methylprednisolone, Methyltestosterone, Methynodiol Diacelate, Methysergide, Methysergide Maleate, Metiamide, Metiapine, Metioprim, metipamide, Metipranolol, Metizoline Hydrochloride, Metkephamid Acetate, metoclopramide, Metocurine Iodide, Metogest, Metolazone, Metopimazine, Metoprine, Metoprolol, Metoprolol tartrate, Metouizine, metrifonate, Metrizamide, Metrizoate Sodium, Metronidazole, Meturedepa, Metyrapone, Metyrosine, Mexiletine Hydrochloride, Mexrenoate Potassium, Mezlocillin, Mianserin Hydrochloride, mibefradil, Mibefradil Dihydrochloride, Mibolerone, michellamine B, Miconazole, microcolin A, Midaflur, Midazolam Hydrochloride, midodrine, mifepristone, Mifobate, miglitol, milacemide, milameline, mildronate, Milenperone, Milipertine, milnacipran, Milrinone, miltefosine, Mimbane Hydrochloride, minaprine, Minaxolone, Minocromil, Minocycline, Minocycline hydrochloride, Minoxidil, Mioflazine Hydrochloride, miokamycin, mipragoside, mirfentanil, mirimostim, Mirincamycin Hydrochloride, Mirisetron Maleate, Mirtazapine, Misonidazole, Misoprostol, Mitindomide, Mitocarcin, Mitocromin, Mitogillin, mitoguazone, mitolactol, Mitomalcin, Mitomycin, mitonafide, Mitosper, Mitotane, mitoxantrone, mivacurium chloride, mivazerol, mixanpril, Mixidine, mizolastine, mizoribine, Moclobemide, modafinil, Modaline Sulfate, Modecamide, moexipril, mofarotene, Mofegiline Hydrochloride, mofezolac, molgramostim, Molinazone, Molindone Hydrochloride, Molsidomine, mometasone, Monatepil Maleate, Monensin, Monoctanoin, montelukast, Montelukast Sodium, montirelin, mopidamol, moracizine, Morantel Tartrate, Moricizine, Morniflumate, Morphine, Morrhuate Sodium, mosapramine, mosapride, motilide, Motretinide, Moxalactam Disodium, Moxazocine, Moxifloxacin, moxiraprine, Moxnidazole, moxonidine, Mumps Skin Test Antigen, Muzolimine, mycaperoxide B, Mycophenolate mofetil, Mycophenolic Acid, myriaporone, Nabazenil, Nabilone, Nabitan Hydrochloride, Naboctate Hydrochloride, Nabumetone, N-acetyldinaline, Nadide, nadifloxacin, Nadolol, nadroparin calcium, nafadotride, nafamostat, nafarelin, Nafcillin Sodium, Nafenopin, Nafimidone Hydrochloride, Naflocort, Nafomine Malate, Nafoxidine Hydrochloride, Nafronyl Oxalate, Naftifine Hydrochloride, naftopidil, naglivan, nagrestip, Nalbuphine Hydrochloride, Nalidixate Sodium, Nalidixic Acid, nalmefene, Nalmexone Hydrochloride, naloxone, Naltrexone, Namoxyrate, Nandrolone Phenpropionate, Nantradol Hydrochloride, Napactadine Hydrochloride, napadisilate, Napamezole Hydrochloride, napaviin, Naphazoline Hydrochloride, naphterpin, Naproxen, Naproxen sodium, Naproxol, napsagatran, Naranol Hydrochloride, Narasin, naratriptan, nartograstim, nasaruplase, natalizumab, Natamycin, nateplase, Naxagolide Hydrochloride, Nebivolol, Nebramycin, nedaplatin, Nedocromil, Nefazodone Hydrochloride, Neflumozide Hydrochloride, Nefopam Hydrochloride, Nelezaprine Maleate, Nemazoline Hydrochloride, nemorubicin, Neomycin Palmitate, Neostigmine Bromide, neridronic acid, Netilmicin Sulfate, Neutramycin, Nevirapin Nexeridine Hydrochloride, Niacin, Nibroxane, Nicardipine Hydrochloride, Nicergoline, Niclosamide, Nicorandil, Nicotinamide, Nicotinyl Alcohol, Nifedipine, Nifirmerone, Nifluridide, Nifuradene, Nifuraldezone, Nifuratel, Nifuratrone, Nifurdazil, Nifurimide, Nifurpirinol, Nifurquinazol, Nifurthiazole, Nifurtimox, nilotinib, nilotinib hydrochloride monohydrate, nilutamide, Nilvadipine, Nimazone, Nimodipine, niperotidine, niravoline, Niridazole, nisamycin, Nisbuterol Mesylate, nisin, Nisobamate, Nisoldipine, Nisoxetin Nisterime Acetate, Nitarsone, nitazoxanide, nitecapone, Nitrafudam Hydrochloride, Nitralamine Hydrochloride, Nitramisole Hydrochloride, Nitrazepam, Nitrendipine, Nitrocydine, Nitrodan, Nitrofurantoin, Nitrofurazone, Nitroglycerin, Nitromersol, Nitromide, Nitromifene Citrate, Nitrous Oxide, nitroxide antioxidant, nitrullyn, Nivazol, Nivimedone Sodium, Nizatidine, Noberastine, Nocodazole, Nogalamycin, Nolinium Bromide, Nomifensine Maleate, Noracymethadol Hydrochloride, Norbolethone, Norepinephrine Bitartrate, Norethindrone, Norethynodrel, Norfurane, Norfloxacin, Norgestimate, Norgestomet, Norgestrel, Nortriptyline Hydrochloride, Noscapine, Novobiocin Nylestriol, Nystatin, Obidoxime Chloride, Ocaperidone, Ocfentanil Hydrochloride, Ocinaplon, Octanoic Acid, Octazamide, Octenidine Hydrochloride, Octodrine, Octreotide, Octriptyline Phosphate, Ofloxacin, Ofornine, okicenone, Olanzepine, Olmesartan, olmesartan medoxomil, olopatadine, olopatadine hydrochloride, olprinone, olsalazine, Olsalazine Sodium, Olvanil, Omalizumab, Omega-3 acid ethyl esters, omeprazole, onapristone, ondansetron, Ontazolast, Oocyte Opipramol Hydrochloride, oracin, Orconazole Nitrate, Orgotein, Orlislat, Ormaplatin, Ormetoprim, Ornidazole, Orpanoxin, Orphenadrine Citrate, osaterone, Oseltamivir, otenzepad, Oxacillin Sodium, Oxagrelate, oxaliplatin, Oxamarin Hydrochloride, oxamisole, Oxamniquine, oxandrolone, Oxantel Pamoate, Oxaprotiline Hydrochloride, Oxaprozin, Oxarbazole, Oxatomide, oxaunomycin, Oxazepam, oxcarbazepine, Oxendolone, Oxethazaine, Oxetorone Fumarate, Oxfendazole, Oxfenicine, Oxibendazole, oxiconazole, Oxidopamine, Oxidronic Acid, Oxifungin Hydrochloride, Oxilorphan, Oximonam, Oximonam Sodium, Oxiperomide, oxiracetam, Oxiramide, Oxisuran, Oxmetidine Hydrochloride, oxodipine, Oxogestone Phenopropionate, Oxolinic Acid, Oxprenolol Hydrochloride, Oxtriphylline, Oxybutynin Chloride, Oxychlorosene, Oxycodone, oxycodone hydrochloride, Oxymetazoline Hydrochloride, oxymetholone, Oxymorphone Hydrochloride, Oxypertine, Oxyphenbutazone, Oxypurinol, Oxytetracycline, Oxytocin, ozagrel, Ozlinone, Paclitaxel, palauamine, Paldimycin, palinavir, Palivizumab, palmitoylrhizoxin, Palmoxirate Sodium, pamaqueside, Pamatolol Sulfate, pamicogrel, Pamidronate Disodium, pamidronic acid, Panadiplon, panamesine, panaxytriol, Pancopride, Pancuronium Bromide, panipenem, pannorin, panomifene, pantethine, pantoprazole, Papaverine Hydrochloride, parabactin, paracetamol, Parachlorophenol, Paraldehyde, Paramethasone Acetate, Paranyline Hydrochloride, Parapenzolate Bromide, Pararosaniline Pamoate, Parbendazole, Parconazole Hydrochloride, Paregoric, Pareptide Sulfate, Pargyline Hydrochloride, parnaparin sodium, Paromomycin Sulfate, Paroxetine, paroxetine hydrochloride, parthenolide, Partricin, Paulomycin, pazelliptine, Pazinaclone, Pazoxide, pazufloxacin, pefloxacin, pegaspargase, Pegorgotein, Pegylated interferon alfa-2a, Pelanserin Hydrochloride, peldesine, Peliomycipelretin, Pelrinone Hydrochloride, Pemedolac, Pemerid Nitrate, Pemetrexed, pemirolast, Pemoline, Penamecillin, Penbutolol Sulfate, Penciclovir, Penfluridol, Penicillamine, Penicillin G Benzathine, Penicillin G Potassium, Penicillin G Procaine, Penicillin G Sodium, Penicillin V Hydrabamine, Penicillin V Benzathine, Penicillin V Potassium, Pentabamate, Pentaerythritol Tetranitrate, pentafuside, pentamidine, pentamorphone, Pentamustine, Pentapiperium Methylsulfate, Pentazocine, Pentetic Acid, Pentiapine Maleate, pentigetide, Pentisomicin, Pentizidone Sodium, Pentobarbital, Pentomone, Pentopril, pentosan, pentostatin, Pentoxifylline, Pentrinitrol, pentrozole, Peplomycin Sulfate, Pepstatin, perflubron, perfofamide, Perfosfamide, pergolide, Perhexyline Maleate, perillyl alcohol, Perindopril, perindoprilat, Perlapin Permethrin, perospirone, Perphenazine, Phenacemide, phenaridine, phenazinomycin, Phenazopyridine Hydrochloride, Phenbutazone Sodium Glycerate, Phencarbamide, Phencyclidine Hydrochloride, Phendimetrazine Tartrate, Phenelzine Sulfate, Phenformin, Phenmetrazine Hydrochloride, Phenobarbital, Phenoxybenzamine Hydrochloride, Phenprocoumon, phenserine, phensuccinal, Phensuximide, Phentermine, Phentermine Hydrochloride, phentolamine mesilate, Phentoxifylline, Phenyl Aminosalicylate, phenylacetate, Phenylalanine, phenylalanylketoconazole, Phenylbutazone, Phenylephrine Hydrochloride, Phenylpropanolamine Hydrochloride, Phenylpropanolamine Polistirex, Phenyramidol Hydrochloride, Phenyloin, Phenyloin sodium, Physostigmine, picenadol, picibanil, Picotrin Diolamine, picroliv, picumeterol, pidotimod, Pifarnine, Pilocarpine, pilsicamide, pimagedine, Pimetine Hydrochloride, pimilprost, Pimobendan, Pimozide, Pinacidil, Pinadoline, Pindolol, pinnenol, pinocebrin, Pinoxepin Hydrochloride, pioglitazone, Pipamperone, Pipazethate, pipecuronium bromide, Piperacetazine, Piperacillin, Piperacillin Sodium, Piperamide Maleate, piperazinc, Pipobroman, Piposulfan, Pipotiazine Palmitate, Pipoxolan Hydrochloride, Piprozolin, Piquindone Hydrochloride, Piquizil Hydrochloride, Piracetam, Pirandamine Hydrochloride, pirarubicin, Pirazmonam Sodium, Pirazolac, Pirbenicillin Sodium, Pirbuterol Acetate, Pirenperone, Pirenzepine Hydrochloride, piretanide, Pirfenidone, Piridicillin Sodium, Piridronate Sodium, Piriprost, piritrexim, Pirlimycin Hydrochloride, pirlindole, pirmagrel, Pirmenol Hydrochloride, Pirnabine, Piroctone, Pirodavir, pirodomast, Pirogliride Tartrate, Pirolate, Pirolazamide, Piroxantrone Hydrochloride, Piroxicam, Piroximone, Pirprofen, Pirquinozol, Pirsidomine, Pivampicillin Hydrochloride, Pivopril, Pizotyline, placetin A, Plicamycin, Plomestane, Pobilukast Edamine, Podofilox, Poisonoak Extract, Poldine Methylsulfate, Poliglusam, Polignate Sodium, Polymyxin B Sulfate, Polythiazide, Ponalrestat, Porfimer Sodium, Porfiromycin, Potassium Chloride, Potassium Iodide, Potassium Permanganate, Povidone-Iodine, Practolol, Pralidoxime Chloride, Pramipexole, Pramiracetam Hydrochloride, Pramoxine Hydrochloride, Pranolium Chloride, Pravadoline Maleate, Pravastatin, Pravastatin sodium, Prazepam, Prazosin, Prazosin Hydrochloride, Prednazate, Prednicarbate, Prednimustine, Prednisolone, prednisolone quetiapine fumerate, Prednisone, Prednival, Pregabalin, Pregnenolone Succiniate, Prenalterol Hydrochloride, Prenylamine, Pridefine Hydrochloride, Prifelone, Prilocalne Hydrochloride, Prilosec, Primaquine Phosphate, Primidolol, Primidone, Prinivil, Prinomide Tromethamine, Prinoxodan, pritosufloxacin, Prizidilol Hydrochloride, Proadifen Hydrochloride, Probenecid, Probicromil Calcium, Probucol, Procainamide Hydrochloride, Procaine Hydrochloride, Procarbazine Hydrochloride, Procaterol Hydrochloride, Prochlorperazine, Procinonide, Proclonol, Procyclidine Hydrochloride, Prodilidine Hydrochloride, Prodolic Acid, Profadol Hydrochloride, Progabide, Progesterone, Proglumide, Proinsulin (human), Proline, Prolintane Hydrochloride, Promazine Hydrochloride, Promethazine, Promethazine hydrochloride, Propafenone Hydrochloride, propagermanium, Propanidid, Propantheline Bromide, Proparacaine Hydrochloride, Propatyl Nitrate, propentofylline, Propenzolate Hydrochloride, Propikacin, Propiomazine, Propionic Acid, propionylcarnitine, propiram, propiram, propiverine, Propofol, Proponolol hydrochloride, Propoxycaine Hydrochloride, Propoxyphene Hydrochloride, Propranolol Hydrochloride, Propulsid, propylbis-acridone, Propylhexedrine, Propyliodone, Propylthiouracil, Proquazone, Prorenoate Potassium, Proroxan Hydrochloride, Proscillaridin, Prostalene, prostratin, Protamine Sulfate, protegrin, Protirelin, Protriptyline Hydrochloride, Proxazole, Proxazole Citrate, Proxicromil, Proxorphan Tartrate, prulifloxacin, pseudoephedrine, Pseudophedrine hydrochloride, Puromycin, Pyrabrom, Pyrantel Pamoate, Pyrazinamide, Pyrazofurin, pyrazoloacridine, Pyridostigmine Bromide, Pyridoxine hydrochloride, Pyrilamine Maleate, Pyrimethamine, Pyrinoline, Pyrithione Sodium, Pyrithione Zinc, Pyrovalerone Hydrochloride, Pyroxamine Maleate, Pyrrocaine, Pyrroliphene Hydrochloride, Pyrrolnitrin, Pyrvinium Pamoate, Quadazocine Mesylate, Quazepam, Quazinone, Quazodine, Quazolast, quetiapine, quetiapine fumarate, quiflapon, quinagolide, Quinaldine Blue, quinapril, Quinapril hydrochloride, Quinazosin Hydrochloride, Quinbolone, Quinctolate, Quindecamine Acetate, Quindonium Bromide, Quinelorane Hydrochloride, Quinestrol, Quinfamide, Quingestanol Acetate, Quingestrone, Quinidine Gluconate, Quinielorane Hydrochloride, Quinine Sulfate, Quinpirole Hydrochloride, Quinterenol Sulfate, Quinuclium Bromide, Quinupristin, Quipazine Maleate, Rabeprazole, Rabeprazole Sodium, Racephenicol, Racepinephrine, Rafoxanide, Ralitoline, raloxifene, raltegravir, raltitrexed, ramatroban, Ramipril, Ramoplanin, ramosetron, ranelic acid, Ranimycin, Ranitidine, Ranitidine hydrochloride, ranolazine, Rauwolfia Serpentina, recainam, Recainam Hydrochloride, Reclazepam, Recombinant factor VIII, regavirumab, Regramostim, Relaxin, Relomycin, Remacemide Hydrochloride, Remifentanil Hydrochloride, Remiprostol, Remoxipride, Repirinast, Repromicin, Reproterol Hydrochloride, Reserpine, resinferatoxin, Resorcinol, retapamulin, retelliptine demethylated, reticulon, reviparin sodium, revizinone, rhenium etidronate, rhizoxin, RI retinamide, Ribaminol, Ribavirin, Riboprine, ricasetron, Ridogrel, Rifabutin, Rifametane, Rifamexil, Rifamide, Rifampin, Rifapentine, Rifaximin, rilopirox, Riluzole, rimantadine, Rimcazole Hydrochloride, Rimexolone, Rimiterol Hydrobromide, Rimonabant, rimoprogin, riodipine, Rioprostil, Ripazepam, ripisartan, Risedronate, Risedronate Sodium, risedronic acid, Risocaine, Risotilide Hydrochloride, rispenzepine, Risperdal, Risperidone, Ritanserin, ritipenem, Ritodrine, Ritolukast, ritonavir, rituximab, rivastigmine, rivastigmine tartrate, Rizatriptan, rizatriptan benzoate, Rocastine Hydrochloride, Rocuronium Bromide, Rodocaine, Roflurane, Rogletimide, rohitukine, rokitamycin, Roletamicide, Rolgamidine, Rolicyprine, Rolipram, Rolitetracycline, Rolodine, Romazarit, romurtide, Ronidazole, Ropinirole, Ropitoin Hydrochloride, ropivacaine, Ropizine, roquinimex, Rosaramicin, rosiglitazone, Rosiglitazone maleate, Rosoxacin, Rosuvastatin, Rotavirus vaccine, rotigotine, Rotoxamine, roxaitidine, Roxarsone, roxindole, roxithromycin, rubiginone B1, ruboxyl, rufloxacin, rupatidine, Rutamycin, ruzadolane, Sabeluzole, safingol, safironil, saintopin, salbutamol, Salbutamol sulfate, Salcolex, Salethamide Maleate, Salicyl Alcohol, Salicylamide, Salicylate Meglumine, Salicylic Acid, Salmeterol, Salnacediin, Salsalate, sameridine, sampatrilat, Sancycline, sanfetrinem, Sanguinarium Chloride, Saperconazole, saprisartan, sapropterin, sapropterin dihydrochloride, saquinavir, Sarafloxacin Hydrochloride, Saralasin Acetate, sarcophytol A, sargramostim, Sarmoxicillin, Sarpicillin, sarpogrelate, saruplase, saterinone, satigrel, satumomab pendetide, Scopafungin, Scopolamine Hydrobromide, Scrazaipine Hydrochloride, Secalciferol, Secobarbital, Seelzone, segiline, Seglitide Acetate, Selegiline Hydrochloride, Selenium Sulfide, Selenomethionine Se-75, Selfotel, sematilide, semduramicin, semotiadil, semustine, Sepazonium Chloride, Seperidol Hydrochloride, Seprilose, Seproxetine Hydrochloride, Seractide Acetate, Sergolexole Maleate, Serine, Sermetacin, Sermorelin Acetate, sertaconazole, sertindole, sertraline, sertraline hydrochloride, S-ethynyluracil, setiptiline, Setoperone, Sevelamer, sevirumab, sevoflurane, sezolamide, Sibopirdine, Sibutramine Hydrochloride, Silandrone, Sildenafil, sildenafil citrate, silipide, silteplase, Silver Nitrate, simendan, Simtrazene, Simvastatin, Sincalide, Sinefungin, sinitrodil, sinnabidol, sipatrigine, sirolimus, Sisomicin, Sitagliptin, Sitogluside, sizofuran, sobuzoxane, Sodium Amylosulfate, Sodium Iodide I-123, Sodium Nitroprusside, Sodium Oxybate, sodium phenylacetate, Sodium Salicylate, Sodium valproate, Solifenacin, solverol, Solypertine Tartrate, Somalapor, Somantadine Hydrochloride, somatomedin B, somatomedin C, Somatostatin, somatrem, somatropin, Somenopor, Somidobove, Sorbinil, Sorivudine, sotalol, Soterenol Hydrochloride, Sparfloxacin, Sparfosate Sodium, sparfosic acid, Sparsomy, Sparteine Sulfate, Spectinomycin Hydrochloride, spicamycin D, Spiperone, Spiradoline Mesylate, Spiramycin, Spirapril Hydrochloride, Spiraprilat, Spirogermanium Hydrochloride, Spiromustine, Spironolactone, Spiroplatin, Spiroxasone, splenopentin, spongistatin, Sprodiamide, squalamine, Stallimycin Hydrochloride, Stannous Pyrophosphate, Stannous Sulfur Colloid, Stanozolol, Statolon, staurosporine, stavudine, Steffimycin, Stenbolone Acetate, stepronin, Stilbazium Iodide, Stilonium Iodide, stipiamide, Stiripentol, stobadine, Streptomycin Sulfate, Streptonicozid, Streptonigrin, Streptozocin, Strontium Chloride Sr-89, succibun, Succimer, Succinylcholine Chloride, Sucralfate, Sucrosofate Potassium, Sudoxicam, Sufentanil, Sufotidine, Sulazepam, Sulbactam Pivoxil, Sulconazole Nitrate, Sulfabenz, Sulfabenzamide, Sulfacetamide, Sulfacytine, Sulfadiazine, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, sulfasalazine, Sulfasomizole, Sulfazamet, Sulfinalol Hydrochloride, sulfinosine, Sulfinpyrazone, Sulfisoxazole, Sulfomethoxazole, Sulfomyxin, Sulfonterol Hydrochloride, sulfoxamine, Sulinldac, Sulmarin, Sulnidazole, Suloctidil, Sulofenur, sulopenem, Suloxifen Oxalate, Sulpiride, Sulprostone, sultamicillin, Sulthiame, sultopride, sulukast, Sumarotene, sumatriptan, Sumatriptan succinate, Suncillin Sodium, Suproclone, Suprofen, suradista, suramin, Surfomer, Suricamide Maleate, Suritozole, Suronacrine Maleate, Suxemerid Sulfate, swainsonine, symakalim, Symclosene, Symetine Hydrochloride, Taciamine Hydrochloride, Tacrine Hydrochloride, Tacrolimus, Tadalafil, Talampicillin Hydrochloride, Taleranol, Talisomycin, tallimustine, Talmetacin, Talniflumate, Talopram Hydrochloride, Talosalate, Tametraline Hydrochloride, Tamoxifen, tamoxifen citrate, Tampramine Fumarate, Tamsulosin, Tamsulosin Hydrochloride, Tandamine Hydrochloride, tandospirone, tapgen, taprostene, Tasosartan, tauromustine, Taxane, Taxoid, Tazadolene Succinate, tazanolast, tazarotene, Tazifylline Hydrochloride, Tazobactam, Tazofelone, Tazolol Hydrochloride, Tebufelone, Tebuquine, Teclozan, Tecogalan Sodium, Teecleukin, Teflurane, Tegafur, Tegaserod, Tegretol, Teicoplanin, telenzepine, tellurapyrylium, telmesteine, telmisartan, Teloxantrone Hydrochloride, Teludipine Hydrochloride, Temafloxacin Hydrochloride, Tematropium Methyl sulfate, Temazepam, Temelastine, temocapril, Temocillin, temoporfin, temozolomide, temsirolimus, Tenidap, Teniposide, Tenofovir, tenosal, tenoxicam, tepirindole, Tepoxalin, Teprotide, terazosin, Terazosin Hydrochloride, Terbinafine, Terbutaline Sulfate, Terconazole, terfenadine, terfiavoxate, terguride, Teriparatide, Teriparatide Acetate, terlakiren, terlipressin, terodiline, Teroxalene Hydrochloride, Teroxirone, tertatolol, Tesicam, Tesimide, Testolactone, Testosterone, Tetracaine, tetrachlorodecaoxide, Tetracycline, Tetracycline hydrochloride, Tetrahydrozoline Hydrochloride, Tetramisole Hydrochloride, Tetrazolast Meglumine, tetrazomine, Tetrofosmin, Tetroquinone, Tetroxoprim, Tetrydamine, thaliblastine, Thalidomide, Theofibrate, Theophylline, Thiabendazole, Thiamiprine, Thiamphenicol, Thiamylal, Thiazesim Hydrochloride, Thiazinamium Chloride, Thiethylperazine, Thiithixene, Thimerfonate Sodium, Thimerosal, thiocoraline, thiofedrine, Thioguanine, thiomarinol, Thiopental Sodium, thioperamide, Thioridazine, Thiotepa, Thiphenamil Hydrochloride, Thiphencillin Potassium, Thiram, Thozalinone, Threonine, Thrombin, thrombopoietin, thymalfasin, thymopentin, thymotrinan, Thyromedan Hydrochloride, Thyroxine, Tiacrilast, Tiacrilast Sodium, tiagabine, Tiamenidine, tianeptine, tiapafant, Tiapamil Hydrochloride, Tiaramide Hydrochloride, Tiazofurin, Tibenelast Sodium, Tibolone, Tibric Acid, Ticabesone Propionate, Ticarbodine, Ticarcillin Cresyl Sodium, Ticlatone, ticlopidine, Ticrynafen, tienoxolol, Tifurac Sodium, Tigemonam Dicholine, Tigestol, Tiletamine Hydrochloride, Tilidine Hydrochloride, tilisolol, tilnoprofenarbamel, Tilorone Hydrochloride, Tiludronate Disodium, tiludronic acid, Timefurone, Timobesone Acetate, Timolol, Timolol meleate, Tinabinol, Timidazole, Tinzaparin Sodium, Tioconazole, Tiodazosin, Tiodonium Chloride, Tioperidone Hydrochloride, Tiopinac, Tiospirone Hydrochloride, Tiotidine, Tiotropium, tiotropium bromide, Tioxidazole, Tipentosin Hydrochloride, tipranavir, Tipredane, Tiprenolol Hydrochloride, Tiprinast Meglumine, Tipropidil Hydrochloride, Tiqueside, Tiquinamide Hydrochloride, tirandalydigin, Tirapazamine, tirilazad, tirofiban, tiropramide, titanocene dichloride, Tixanox, Tixocortol Pivalate, Tizanidine Hydrochloride, Tnmethobenzamide Hydrochloride, Tobramycin, Tocamide, Tocamphyl, Tofenacin Hydrochloride, Tolamolol, Tolazamide, Tolazoline Hydrochloride, Tolbutamide, Tolcapone, Tolciclate, Tolfamide, Tolgabide, Tolimidone, Tolindate, Tolmetin, Tolnaftate, Tolpovidone, Tolpyrramide, Tolrestat, Tolterodine, tolterodine tartrate, Tomelukast, Tomoxetine Hydrochloride, Tonazocine Mesylate, Topiramate, topotecan, Topotecan Hydrochloride, topsentin, Topterone, Toquizine, torasemide, toremifene, Torsemide, Tosifen, Tosufloxacin, totipotent stem cell factor (TSCF), Tracazolate, trafermin, Tralonide, Tramadol, Tramadol Hydrochloride, Tramazoline Hydrochloride, trandolapril, Tranexamic Acid, Tranilast, Transcamide, trastuzumab, traxanox, Trazodone Hydrochloride, Trebenzomine Hydrochloride, Trefentanil Hydrochloride, Treloxinate, Trepipam Maleate, Trestolone Acetate, tretinoin, Triacetin, triacetyluridine, Triafungin, Triamcinolone, Triampyzine Sulfate, Triamterene, Triazolam, Tribenoside, tricaprilin, Tricetamide, Trichlormethiazide, trichohyalin, triciribine, Tricitrates, Triclofenol piperazine, Triclofos Sodium, trientine, Trifenagrel, triflavin, Triflocin, Triflubazam, Triflumidate, Trifluoperazine Hydrochloride, Trifluperidol, Triflupromazine, Triflupromazine Hydrochloride, Trifluridine, Trihexyphenidyl Hydrochloride, Trilostane, Trimazosin Hydrochloride, trimegestone, Trimeprazine Tartrate, Trimethadione, Trimethaphan Camsylate, Trimethoprim, Trimetozine, Trimetrexate, Trimipramine, Trimoprostil, Trimoxamine Hydrochloride, Triolein, Trioxifene Mesylate, Tripamide, Tripelennamine Hydrochloride, Triprolidine Hydrochloride, Triptorelin, Trisulfapyrimidines, Troclosene Potassium, troglitazone, Trolamine, Troleandomycin, trombodipine, trometamol, Tropanserin Hydrochloride, Tropicamide, tropine, tropisetron, trospectomycin, trovafloxacin, trovirdine, Tryptophan, Tuberculin, Tubocurarine Chloride, Tubulozole Hydrochloride, tucarcsol, tulobuterol, turosteride, Tybamate, tylogenin, Tyropanoate Sodium, Tyrosine, Tyrothricin, tyrphostins, ubenimex, Uldazepam, Undecylenic Acid, Uracil Mustard, urapidil, Urea, Uredepa, uridine triphosphate, Urofollitropin, Urokinase, Ursodiol, valaciclovir, Valacyclovir hydrochloride, Valine, Valnoctamide, Valproate semisodium, Valproic Acid, valsartan, vamicamide, vanadeine, Vancomycin, vaminolol, Vapiprost Hydrochloride, Vapreotide, Vardenafil, Varenicline, variolin B, Vasopressin, Vecuronium Bromide, velaresol, Velnacrine Maleate, venlafaxine, Venlafaxine hydrochloride, Veradoline Hydrochloride, veramine, Verapamil Hydrochloride, verdins, Verilopam Hydrochloride, Verlukast, Verofylline, veroxan, verteporfin, Vesnarinone, vexibinol, Vidarabine, vigabatrin, vildagliptin, Viloxazine Hydrochloride, Vinblastine Sulfate, vinburnine citrate, Vincofos, vinconate, Vincristine Sulfate, Vindesine, Vindesine Sulfate, Vinepidine Sulfate, Vinglycinate Sulfate, Vinleurosine Sulfate, vinorelbine, vinpocetine, vintoperol, vinxaltine, Vinzolidine Sulfate, Viprostol, Virginiamycin, Viridofulvin, Viroxime, vitaxin, Voglibose, Volazocine, voriconazole, vorozole, voxergolide, Wafarin, Xamoterol, Xanomeline, Xanoxate Sodium, Xanthinol Niacinate, xemiloflban, Xenalipin, Xenbucin, Xilobam, ximoprofen, Xipamide, Xorphanol Mesylate, Xylamidine Tosylate, Xylazine Hydrochloride, Xylometazoline Hydrochloride, xylose, yangambin, zabicipril, zacopride, zafirlukast, Zalcitabine, Zaleplon, zalospirone, Zaltidine Hydrochloride, zaltoprofen, zanamivir, zankiren, zanoterone, Zantac, Zarirlukast, zatebradine, zatosetron, Zatosetron Maleate, zenarestat, Zenazocine Mesylate, Zeniplatin, Zeranol, Zidometacin, Zidovudine, zifrosilone, Zilantel, zilascorb, zileuton, Zimeldine Hydrochloride, Zinc Undecylenate, Zindotrine, Zinoconazole Hydrochloride, Zinostatin, Zinterol Hydrochloride, Zinviroxime, ziprasidone, Zobolt, Zofenopril Calcium, Zofenoprilat, Zolamine Hydrochloride, Zolazepam Hydrochloride, Zoledronate, Zolertine Hydrochloride, zolmitriptan, zolpidem, Zomepirac Sodium, Zometapine, Zoniclezole Hydrochloride, Zonisamide, zopiclone, Zopolrestat, Zorbamyciin, Zorubicin Hydrochloride, zotepine, Zucapsaicin, and pharmaceutically acceptable salts thereof.

REFERENCES

The following references are incorporated herein by reference:

The Journal of Urology, Vol. 160, 1572-1575, October 1998; Sato "Restoration of Sexual Behavior and Dopaminergic Neurotransmission by Long Term Exogenous Testosterone Replacement in Male Rats."

Yonago Acta medica 2005; 48:93-99; S. Morizane "Effects of Testosterone Replacement on Lower Urinary Tract Functions in Elderly Male Rats."

U.S. Patent Publication 20100152699

WIPO Patent Publication WO/2011/146699

The invention claimed is:

1. A device for administering a therapeutic agent, the device comprising:
   an implantable device comprising a reservoir;
   a channeled member in fluid communication with the reservoir; and
   a compound comprising the therapeutic agent and a solubilizer disposed within the reservoir and in fluid communication with the channeled member, wherein:
   the solubilizer comprises an oil;
   the channeled member comprises a nanochannel; and
   the nanochannel has a dimension in the range of 150-250 nm.

2. The device of claim 1 wherein the compound comprises a testosterone ether, ester, or salt.

3. The device of claim 1 wherein the solubilizer further comprises at least one of: Gelucire 44/14, Gelucire 50/13, Peceol, Labrafil M2125 CS, Labrafil M1944 CS, Labrasol, Tween 80, Crodasol, Brij 30, Glycerox 767, NOVOL (Oleyl Alcohol), ETOCAS (PEG-35 Castor Oil), Arlosolve (Dimethyl lsosobride), PEG300, Maisine 35-1, Transcutol HP, Glycerin, Span 80, Span 85, Compritol 888, Propylene Glycol, Dibutyl Sebacate, Triacetin, Miglyol 810, Miglyol 812, Myvacet, Softigen 701, Softigen 767, Kolliphor HS15, Kolliphor RH40, Kolliphor ELP, Stearic Acid, Cetyl Palmitate, Lauroglycol 90, Lauroglycol FCC, Labrafac PG, Labrafac Lipophile WL 1349, Miranol, soybean oil, corn oil, olive oil, castor oil, sesame oil, light mineral oil, heavy mineral oil, coconut oil, canola oil, dimethyl sulfoxide (DMSO), N-Methylpyrrolidone (NMP), Benzyl Benzoate, Capryol PGMC, Glyceryl Monostearate, Vitamin E TPGS and Benzyl Alcohol.

4. The device of claim 1 wherein the channeled member comprises microchannels.

5. The device of claim 1 wherein the device comprises an injection port.

6. The device of claim 1 wherein the device comprises a vent.

7. A method of administering a therapeutic agent, the method comprising:
   inserting a device into an area of a human and or animal anatomy, wherein the device comprises:
   a reservoir;
   a channeled member in fluid communication with the reservoir; and
   a compound comprising the therapeutic agent and a solubilizer disposed within the reservoir and in fluid communication with the channeled member, wherein:
   the solubilizer comprises an oil;
   the channeled member comprises a nanochannel; and
   the nanochannel has a dimension in the range of 150-250 nm; and
   releasing at least a portion of the therapeutic agent and a portion of the solubilizer comprising the oil from the device into the area of the human or animal anatomy.

8. The method of claim 7 wherein the device is configured to release the therapeutic agent at a substantially constant release rate for a dosage period of at least one month.

9. The method of claim 7 wherein the device is configured to release the therapeutic agent at a substantially constant release rate for a dosage period of at least six months.

10. The method of claim 7, wherein the device is configured to release the therapeutic agent at a substantially constant release rate for a dosage period of at least one year.

11. The method of claim 7 wherein the compound comprises a testosterone ether, ester, or salt.

12. The method of claim 7 wherein the solubilizer further comprises at least one of: Gelucire 44/14, Gelucire 50/13, Peceol, Labrafil M2125 CS, Labrafil M1944 CS, Labrasol, Tween 80, Crodasol, Brij 30, Glycerox 767, NOVOL (Oleyl Alcohol), ETOCAS (PEG-35 Castor Oil), Arlosolve (Dimethyl Isosobride), PEG300, Maisine 35-1, Transcutol HP, Glycerin, Span 80, Span 85, Compritol 888, Propylene Glycol, Dibutyl Sebacate, Triacetin, Miglyol 810, Miglyol 812, Myvacet, Softigen 701, Softigen 767, Kolliphor HS15, Kolliphor RH40, Kolliphor ELP, Stearic Acid, Cetyl Palmitate, Lauroglycol 90, Lauroglycol FCC, Labrafac PG, Labrafac Lipophile WL 1349, Miranol, soybean oil, corn oil, olive oil, castor oil, sesame oil, light mineral oil, heavy mineral oil, coconut oil, canola oil, dimethyl sulfoxide (DMSO), N-Methylpyrrolidone (NMP), Benzyl Benzoate, Capryol PGMC, Glyceryl Monostearate, Vitamin E TPGS and Benzyl Alcohol.

* * * * *

UNITED STATES PATENT AND TRADEMARK OFFICE
CERTIFICATE OF CORRECTION

PATENT NO. : 10,369,340 B2
APPLICATION NO. : 14/908157
DATED : August 6, 2019
INVENTOR(S) : Michael Crowley et al.

It is certified that error appears in the above-identified patent and that said Letters Patent is hereby corrected as shown below:

In the Specification

Column 2, Line 59, delete "Dimethyl lsosobride" and insert --Dimethyl Isosorbide-- therefor.

Column 3, Lines 62-63, delete "Dimethyl lsosobride" and insert --Dimethyl Isosorbide-- therefor.

Column 4, Line 47, delete "Dimethyl lsosobride" and insert --Dimethyl Isosorbide-- therefor.

In the Claims

Claim 3, Column 27, Lines 57-58, delete "Dimethyl lsosobride" and insert --Dimethyl Isosorbide-- therefor.

Claim 12, Column 28, Lines 49-50, delete "Dimethyl Isosobride" and insert --Dimethyl Isosorbide-- therefor.

Signed and Sealed this
Eighth Day of October, 2019

Andrei Iancu
*Director of the United States Patent and Trademark Office*